(12) United States Patent
Unsworth

(10) Patent No.: US 10,695,139 B2
(45) Date of Patent: *Jun. 30, 2020

(54) ROBOTIC SYSTEM DISPLAY SYSTEM FOR DISPLAYING AUXILIARY INFORMATION

(71) Applicant: TITAN MEDICAL INC., Toronto (CA)

(72) Inventor: John D. Unsworth, Hamilton (CA)

(73) Assignee: Titan Medical Inc., Toronto, Ontario (CA)

( * ) Notice: Subject to any disclaimer, the term of this patent is extended or adjusted under 35 U.S.C. 154(b) by 0 days.

This patent is subject to a terminal disclaimer.

(21) Appl. No.: 16/455,192

(22) Filed: Jun. 27, 2019

(65) Prior Publication Data

US 2019/0314095 A1 Oct. 17, 2019

Related U.S. Application Data

(63) Continuation of application No. 16/160,200, filed on Oct. 15, 2018, now Pat. No. 10,357,319, which is a
(Continued)

(51) Int. Cl.
*A61B 34/30* (2016.01)
*A61B 34/20* (2016.01)
(Continued)

(52) U.S. Cl.
CPC .............. *A61B 34/30* (2016.02); *A61B 34/10* (2016.02); *A61B 34/20* (2016.02); *A61B 34/25* (2016.02); *A61B 34/37* (2016.02); *A61B 34/70* (2016.02); *A61B 34/74* (2016.02); *A61B 34/76* (2016.02); *A61B 90/06* (2016.02); *A61B 90/361* (2016.02); *G01D 5/262* (2013.01); *G06F 3/016* (2013.01); *G06F 3/0308* (2013.01);
(Continued)

(58) Field of Classification Search
CPC ......... A61B 34/10; A61B 34/20; A61B 34/25; A61B 34/30; A61B 34/37; A61B 34/70; A61B 34/74; A61B 34/76; A61B 90/06; A61B 90/361; A61B 2034/107; A61B 2034/2051; G06F 19/3418; G06F 3/016; G06F 3/0325; G06F 3/0308; G01D 5/262; G06T 11/00; H05K 999/99
USPC ...................................... 382/128, 153; 606/1
See application file for complete search history.

(56) References Cited

U.S. PATENT DOCUMENTS

| 5,808,665 A | 9/1998 | Green |
| 6,246,200 B1 | 6/2001 | Blumenkranz |

(Continued)

FOREIGN PATENT DOCUMENTS

WO WO199501757 1/1995

OTHER PUBLICATIONS

Non-Final Rejection dated Oct. 12, 2016 for U.S. Appl. No. 15/211,295.

*Primary Examiner* — Daniel G Mariam
(74) *Attorney, Agent, or Firm* — Knobbe Martens Olson & Bear LLP

(57) ABSTRACT

A Robotic control system has a wand, which emits multiple narrow beams of light, which fall on a light sensor array, or with a camera, a surface, defining the wand's changing position and attitude which a computer uses to direct relative motion of robotic tools or remote processes, such as those that are controlled by a mouse, but in three dimensions and motion compensation means and means for reducing latency.

20 Claims, 21 Drawing Sheets

Related U.S. Application Data continuation of application No. 15/490,098, filed on Apr. 18, 2017, now Pat. No. 10,130,434, which is a continuation of application No. 15/211,295, filed on Jul. 15, 2016, now Pat. No. 9,681,922, which is a continuation of application No. 14/831,045, filed on Aug. 20, 2015, now Pat. No. 9,421,068, which is a continuation of application No. 14/302,723, filed on Jun. 12, 2014, now Pat. No. 9,149,339, which is a continuation of application No. 12/449,779, filed as application No. PCT/CA2008/000392 on Feb. 29, 2008, now Pat. No. 8,792,688.

(60) Provisional application No. 60/904,187, filed on Mar. 1, 2007, provisional application No. 60/921,467, filed on Apr. 3, 2007, provisional application No. 60/907,723, filed on Apr. 13, 2007, provisional application No. 60/933,948, filed on Jun. 11, 2007, provisional application No. 60/937,987, filed on Jul. 2, 2007, provisional application No. 61/001,756, filed on Nov. 5, 2007.

(51) Int. Cl.
| | | |
|---|---|---|
| *A61B 34/00* | (2016.01) | |
| *A61B 90/00* | (2016.01) | |
| *A61B 34/37* | (2016.01) | |
| *A61B 34/10* | (2016.01) | |
| *G01D 5/26* | (2006.01) | |
| *G06F 3/01* | (2006.01) | |
| *G06F 3/03* | (2006.01) | |
| *G06T 11/00* | (2006.01) | |
| *A61B 17/00* | (2006.01) | |

(52) U.S. Cl.
CPC ............ *G06F 3/0325* (2013.01); *G06T 11/00* (2013.01); *H05K 999/99* (2013.01); *A61B 90/36* (2016.02); *A61B 2017/00207* (2013.01); *A61B 2017/00703* (2013.01); *A61B 2034/107* (2016.02); *A61B 2034/2051* (2016.02); *A61B 2034/2055* (2016.02); *A61B 2034/2068* (2016.02); *A61B 2090/062* (2016.02); *A61B 2090/365* (2016.02)

(56) References Cited

U.S. PATENT DOCUMENTS

| | | |
|---|---|---|
| 6,249,944 B1 | 7/2001 | Margulis |
| 6,285,902 B1 | 9/2001 | Kienzle |
| 6,470,207 B1 | 10/2002 | Simon |
| 6,554,844 B2 | 4/2003 | Lee |
| 6,621,921 B1 | 9/2003 | Matsugu |
| 6,786,896 B1 | 9/2004 | Madhani |
| 6,917,827 B2 | 7/2005 | Kienzle |
| 7,225,012 B1 | 5/2007 | Susli |
| 7,499,027 B2 | 3/2009 | Bringham |
| 7,625,335 B2 | 12/2009 | Deichmann |
| 7,720,521 B2 | 5/2010 | Cheng |
| 7,747,311 B2 | 6/2010 | Quaid |
| 7,831,292 B2 | 11/2010 | Quaid |
| 8,241,271 B2 | 8/2012 | Millman |
| 8,594,841 B2 | 11/2013 | Zhao |
| 8,600,551 B2 | 12/2013 | Itkowitz |
| 8,706,301 B2 | 4/2014 | Zhao |
| 8,792,688 B2 | 7/2014 | Unsworth |
| 9,149,339 B2 | 10/2015 | Unsworth |
| 9,421,068 B2 | 8/2016 | Unsworth |
| 9,681,922 B2 | 6/2017 | Unsworth |
| 10,130,434 B2 | 11/2018 | Unsworth |
| 2004/0044295 A1 | 3/2004 | Reinert |
| 2005/0261550 A1 | 11/2005 | Akimoto |
| 2006/0017720 A1 | 1/2006 | Li |
| 2007/0021738 A1 | 1/2007 | Nasser |
| 2007/0144298 A1 | 6/2007 | Miller |
| 2009/0131955 A1 | 5/2009 | Wenderow |
| 2011/0060214 A1 | 3/2011 | Makower |
| 2019/0046280 A1 | 2/2019 | Unsworth |

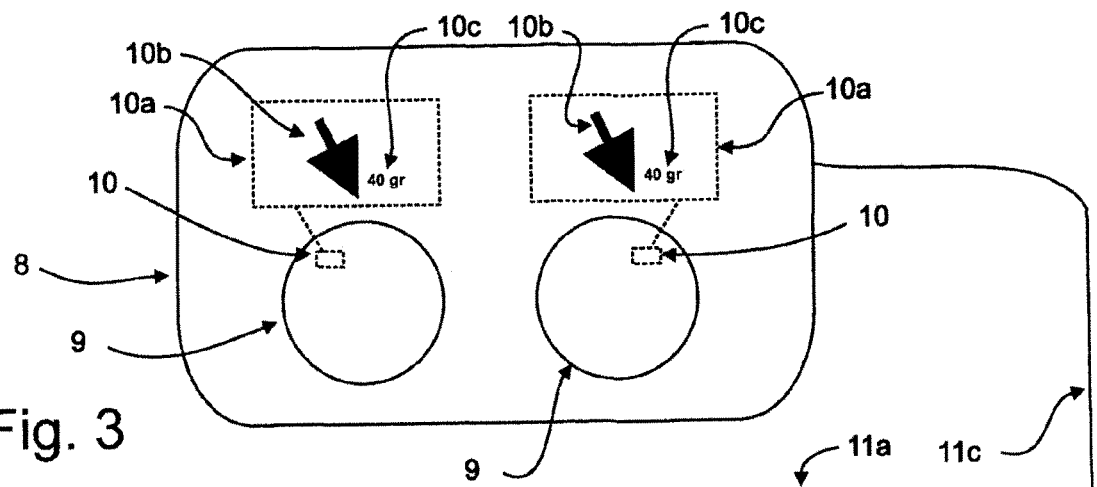
Fig. 3
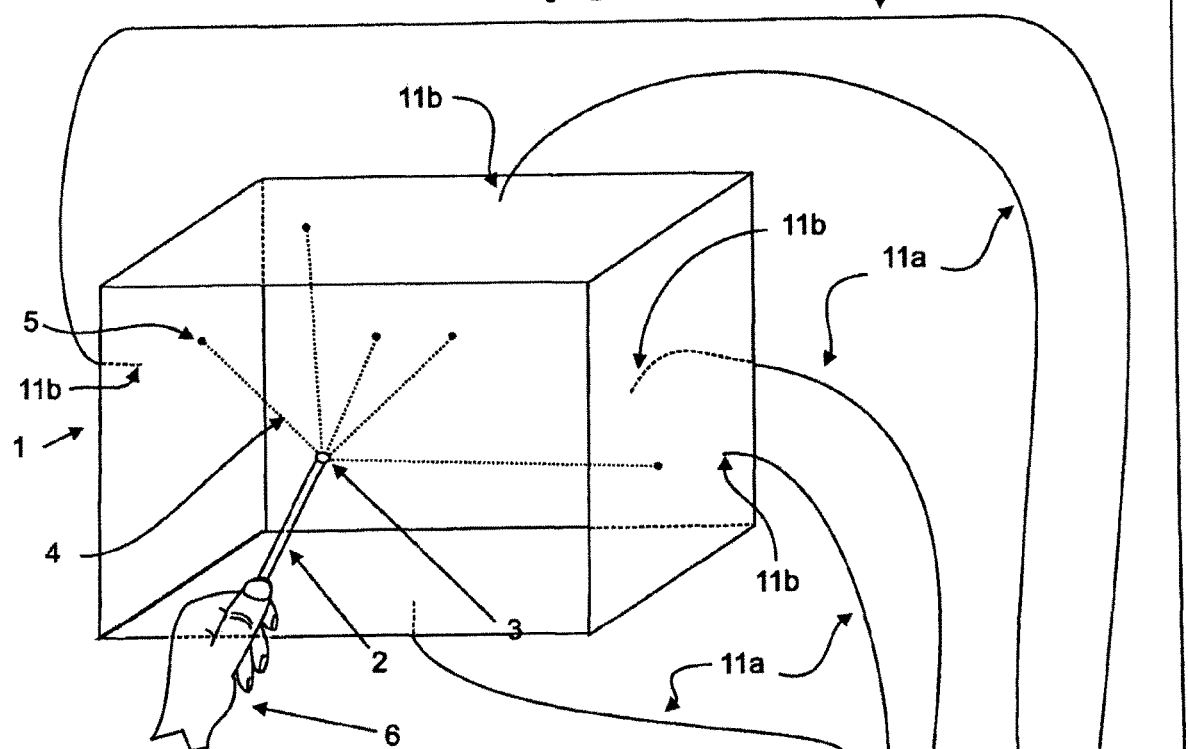
Fig. 4    Fig. 5
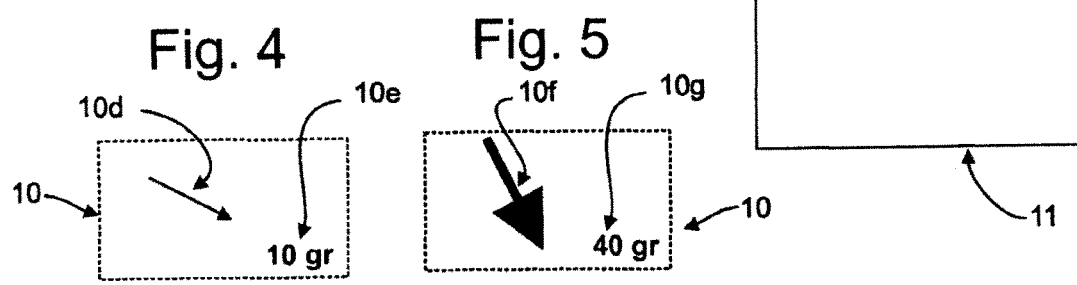

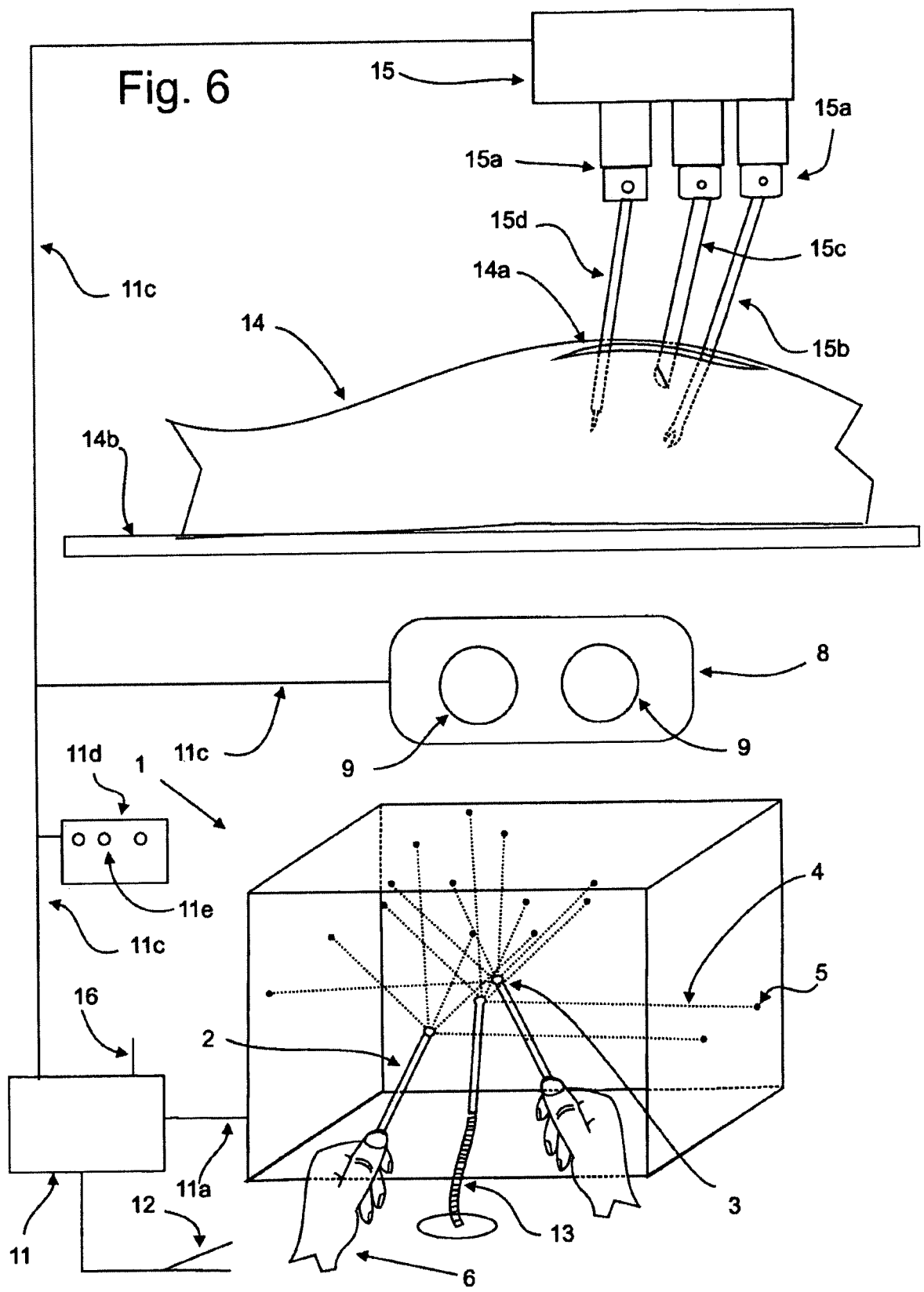

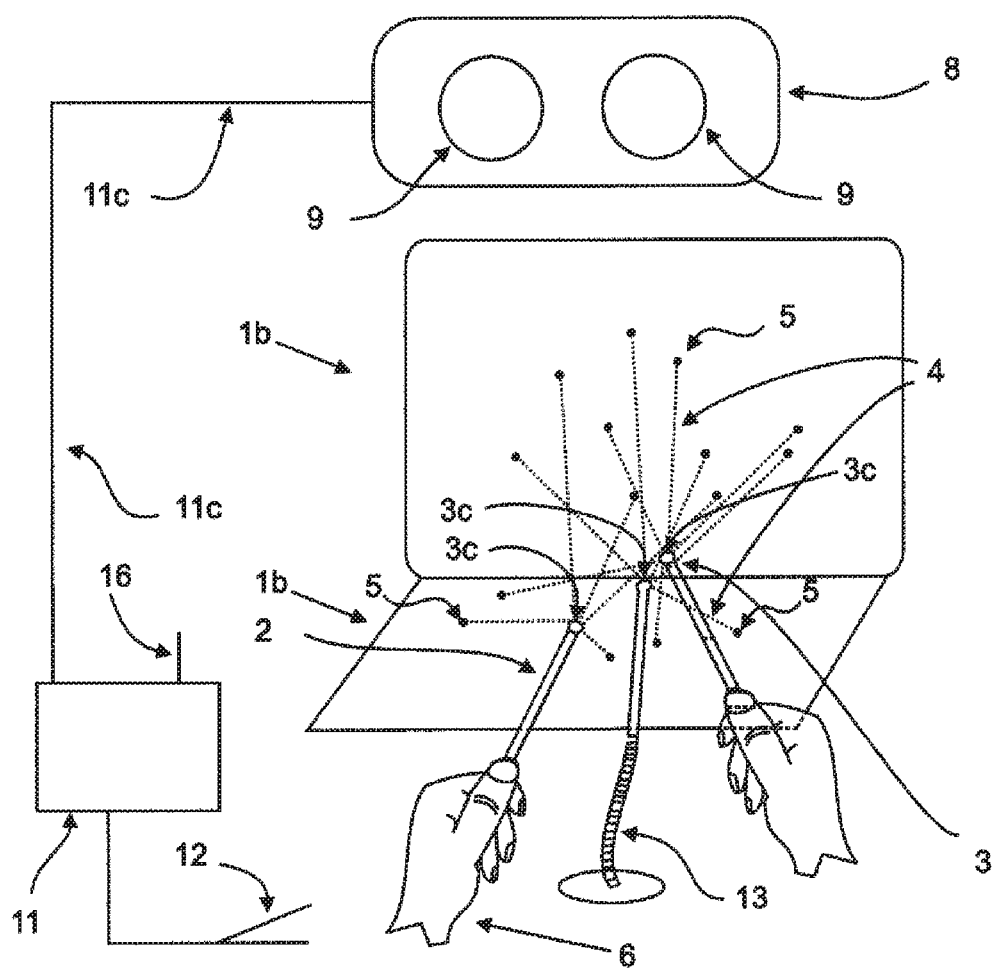
Fig. 6a1

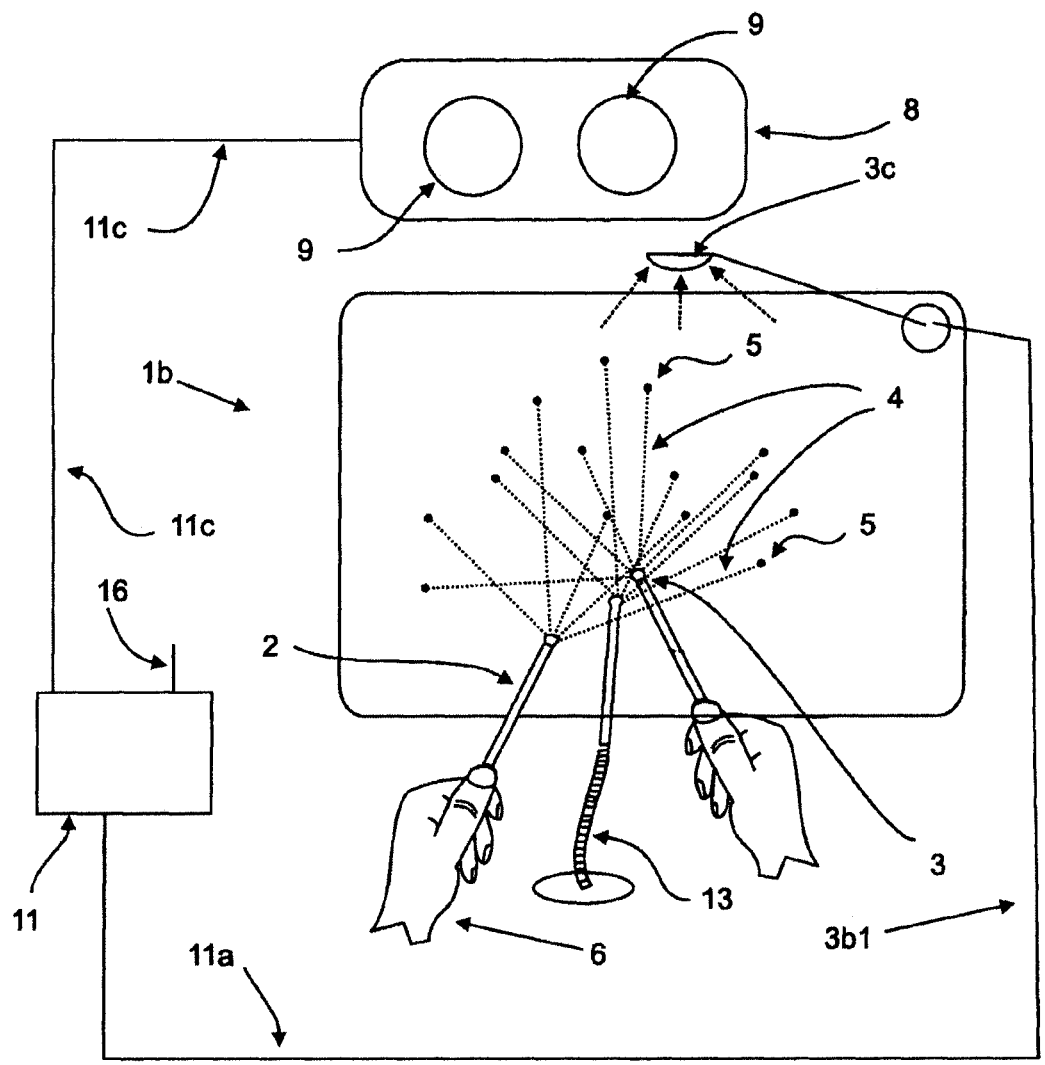
Fig. 6a2

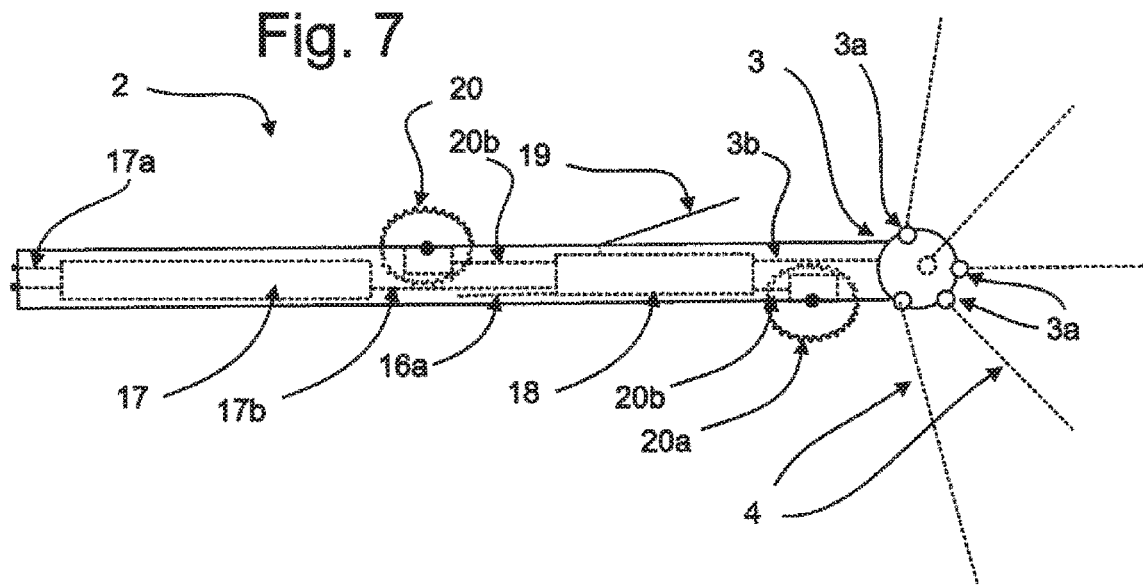
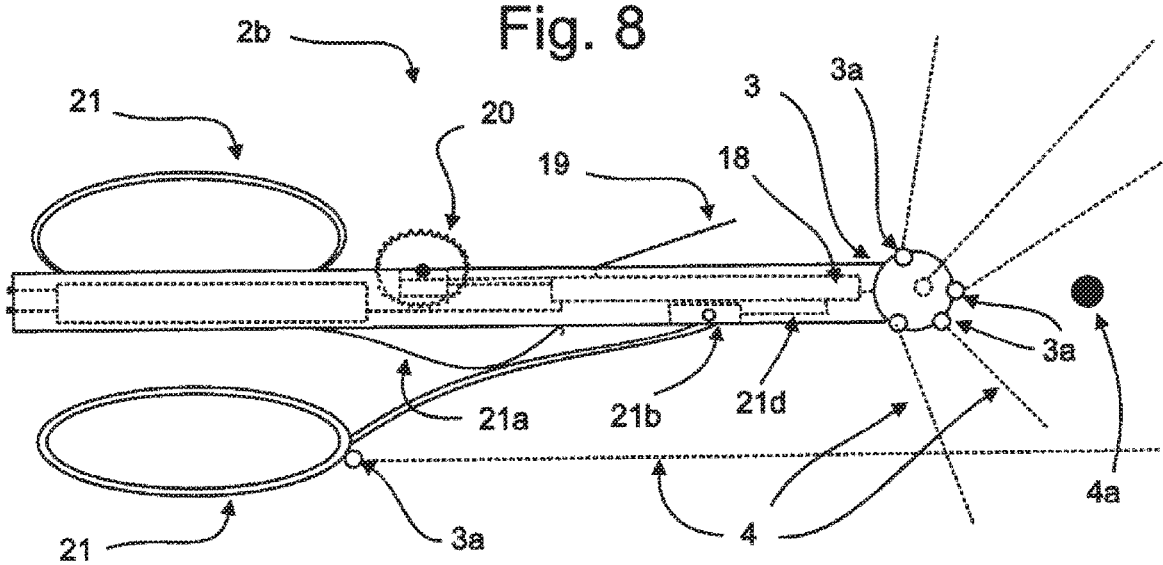

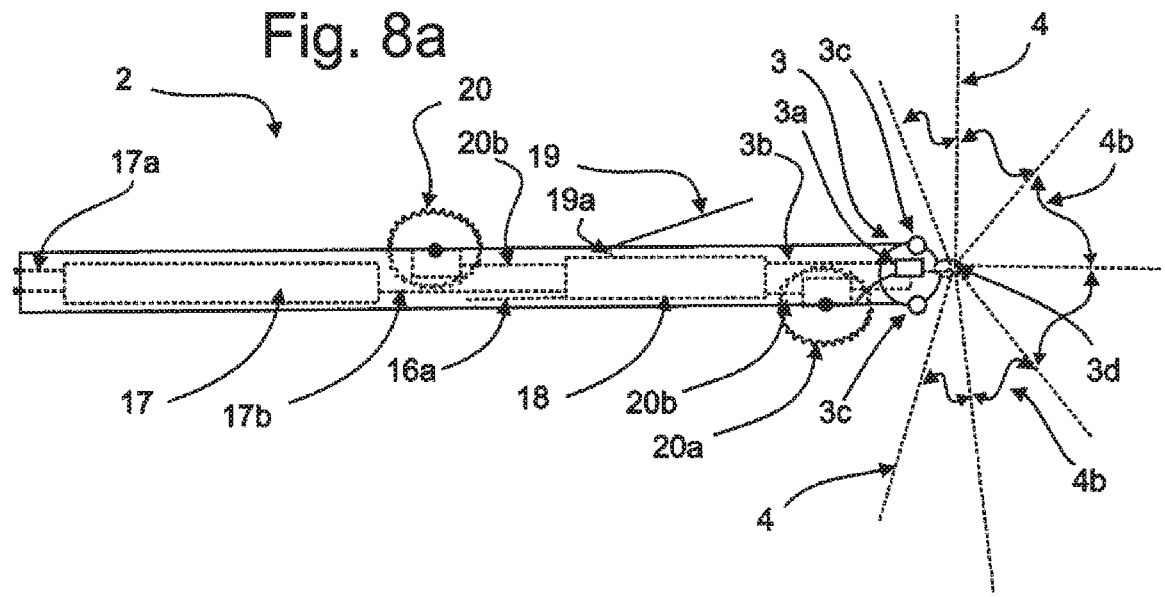
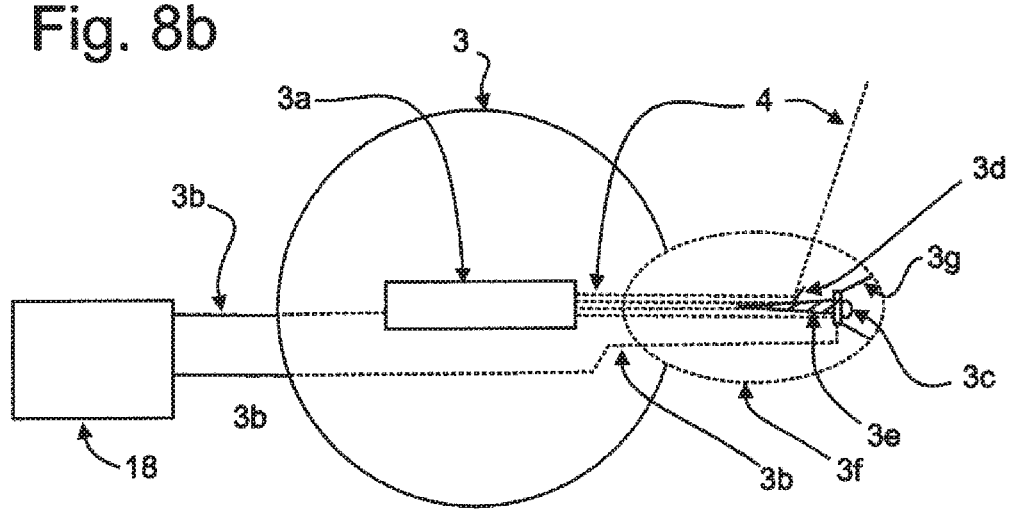

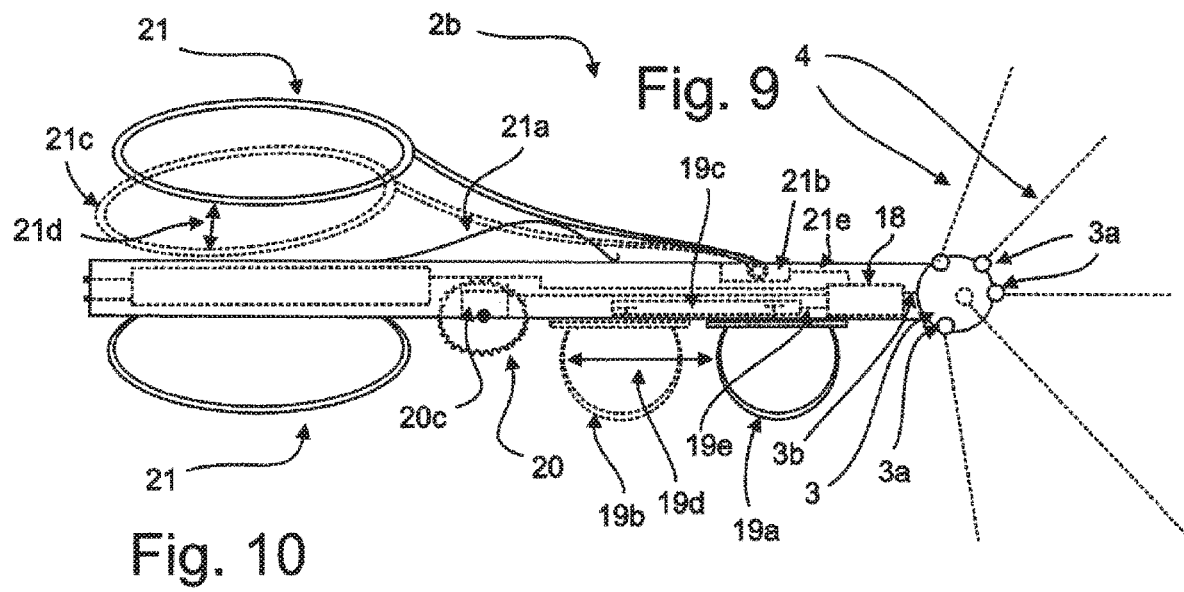
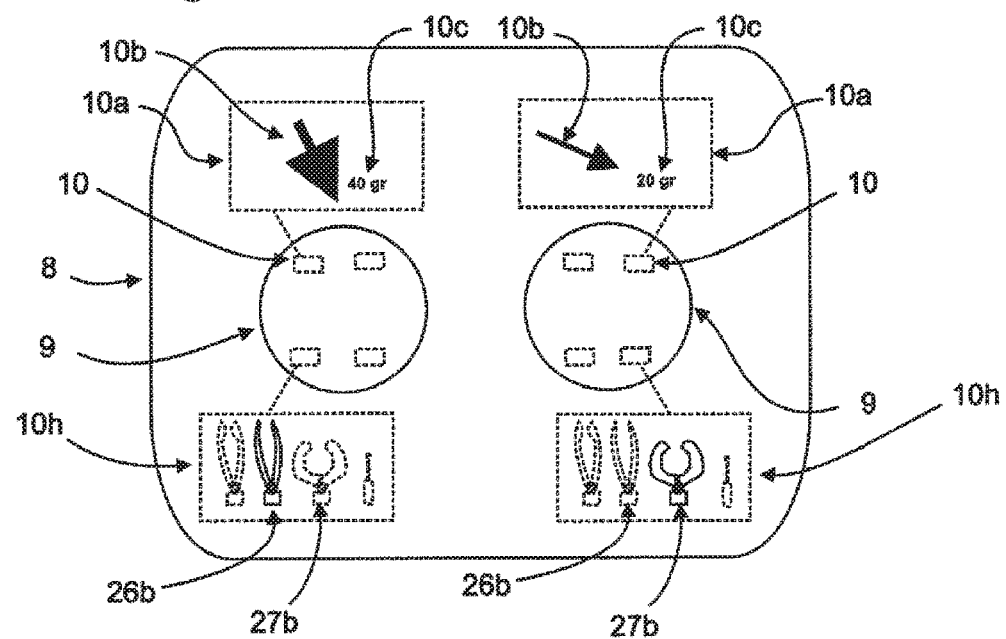
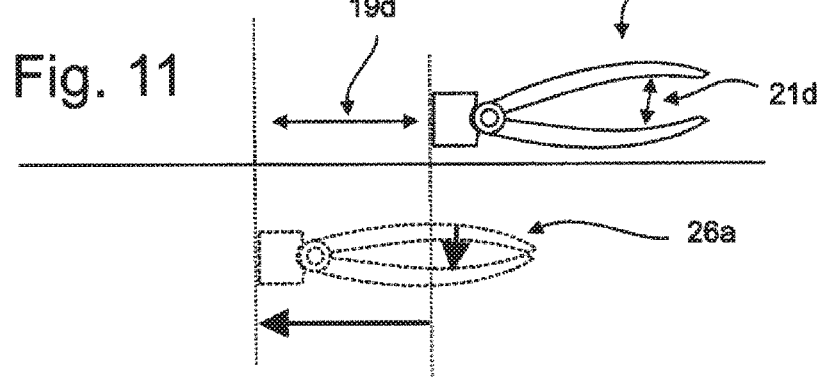

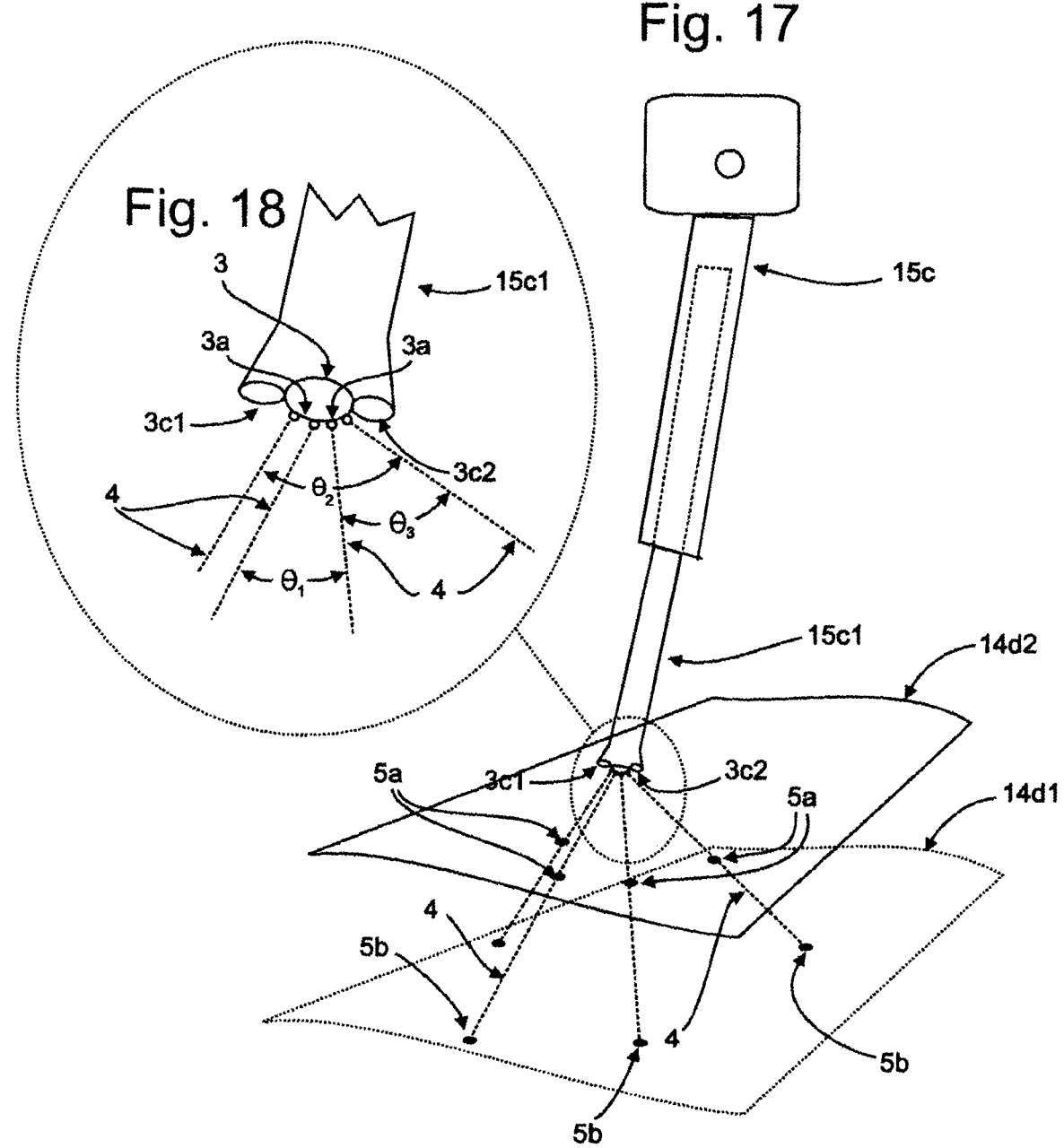

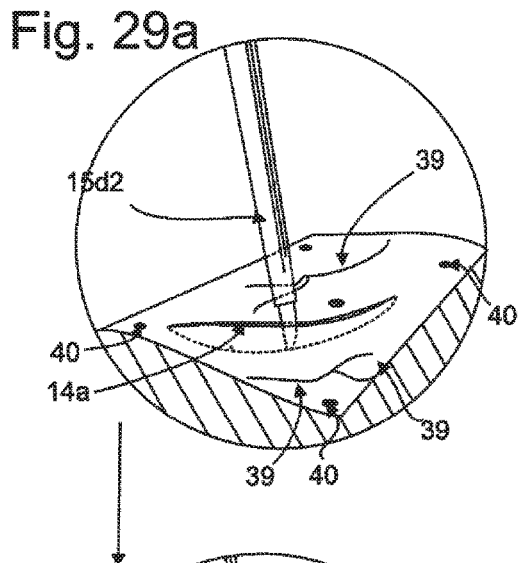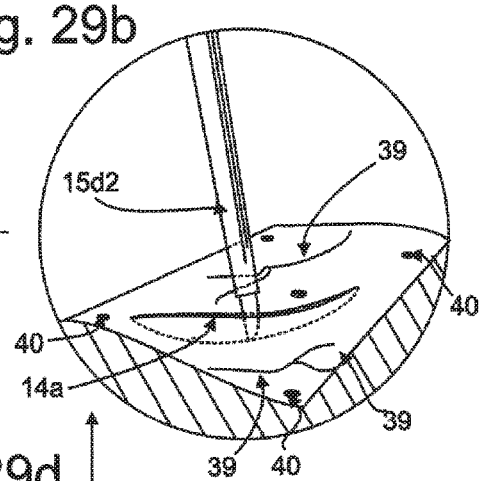

ROBOTIC SYSTEM DISPLAY SYSTEM FOR DISPLAYING AUXILIARY INFORMATION

CROSS-REFERENCE TO RELATED APPLICATIONS

This application is a continuation of U.S. patent application Ser. No. 16/160,200, filed Oct. 15, 2018, which is a continuation of which is U.S. patent application Ser. No. 15/490,098, filed Apr. 18, 2017, which is a continuation of U.S. patent application Ser. No. 15/211,295, filed Jul. 15, 2016, which is continuation of U.S. patent application Ser. No. 14/831,045, filed Aug. 20, 2015, which is a continuation of U.S. patent application Ser. No. 14/302,723 filed Jun. 12, 2014, which is a continuation of U.S. patent application Ser. No. 12/449,779 filed Aug. 25, 2009 which is a 371 of International Patent Application No. PCT/CA2008/000392 filed Feb. 29, 2008, which claims the benefit of the filing dates of U.S. Patent Application No. 60/904,187 filed 1 Mar. 2007 under the title LIGHT SENSOR ARRAY FORMING CAGE AROUND OPERATOR MANIPULATED WAND USED FOR CONTROL OF ROBOT OR REMOTE PROCESSES; U.S. Patent Application No. 60/921,467 filed 3 Apr. 2007 under the title OPERATOR MANIPULATED WAND WHICH CASTS BEAM ONTO LIGHT SENSOR ARRAY FOR CONTROL OF ROBOT OR REMOTE PROCESSES, WITH HAPTIC FEEDBACK; U.S. Patent Application No. 60/907,723 filed 13 Apr. 2007 under the title OPERATOR MANIPULATED WAND WHICH CASTS BEAM ONTO LIGHT SENSOR ARRAY OR SURFACE FOR CONTROL OF ROBOT OR REMOTE PROCESSES, WITH OR WITHOUT HAPTIC FEEDBACK; U.S. Patent Application No. 60/933,948 filed 11 Jun. 2007 under the title OPERATOR MANIPULATED WAND WHICH CASTS BEAM(S) ONTO LIGHT SENSOR ARRAY OR SURFACE FOR CONTROL OF ROBOT OR REMOTE PROCESSES IN THREE DIMENSIONS, WITH HAPTIC FEEDBACK AND MOTION COMPENSATION; U.S. Patent Application No. 60/937,987 filed 2 Jul. 2007 under the title OPERATOR MANIPULATED WAND WHICH CASTS BEAM(S) OR SHAPES ONTO LIGHT SENSOR ARRAY OR SURFACE FOR CONTROL OF ROBOT OR REMOTE PROCESSES IN THREE DIMENSIONS, WITH HAPTIC FEEDBACK AND MOTION COMPENSATION; and U.S. Patent Application No. 61/001,756 filed 5 Nov. 2007 under the title OPERATOR MANIPULATED WAND WHICH CASTS BEAM(S) OR SHAPES ONTO LIGHT SENSOR ARRAY OR SURFACE FOR CONTROL OF ROBOT OR REMOTE PROCESSES IN THREE DIMENSIONS, WITH HAPTIC FEEDBACK, MOTION AND LATENCY COMPENSATION. The content of these patent applications is hereby expressly incorporated by reference into the detailed description hereof.

FIELD OF INVENTION

This invention relates to operator interfaces for controlling robots and remote processes, including pointing devices, such as a mouse. It also relates to methods and systems for controlling remote processes.

BACKGROUND OF THE INVENTION

Real-time operator control of robots has been accomplished with electro-mechanical controls such as joysticks and multiple axis hand grips. These devices suffer from a limited range of motion due to being constrained by the geometry of the control device. In other applications, such as surgery, the operator's hand and finger motions used to operate the device do not closely approximate those motions he would use in conducting the operation by hand. This requires the surgeon to use a different repertoire of hand motions for the robot control, than he would for conducting the operation by hand. Other devices such as a glove actuator, while more closely approximating the actual motion of the hand, suffers from a lack of accuracy regarding the motion of the instrument the hand and fingers grasp, and it is the working end of the instrument which is being mimicked by the robot's tools that do the work. Other interfaces have been developed that rely on multiple cameras to record the motion of the operator's hands with or without faux instruments, but these can also suffer from a lack of accuracy.

These devices also suffer from mechanical wear and tear, which compromises accuracy and require maintenance.

These devices suffer from latency, especially when the operator is separated from the worksite by sufficient distances that there is a significant delay in transmission.

It is an object of some aspects of the invention to address one or more of the above existing concerns.

Other concerns may be also be addressed in those aspects, or separately in other aspects of the invention as will be evident from the remainder of this specification.

SUMMARY OF THE INVENTION

In a first aspect the invention provides a method comprising the steps of actively generating an image pattern on a surface of a first object, detecting the image pattern on the surface of the first object, wherein either the step of actively generating or the step of detecting is performed at a second object spaced away from the first object, and determining parameters of the relative poses of the second object and the surface utilizing the detected image pattern and utilizing reference data for actively generating the image pattern.

The method may further comprise the step of actively displaying on the first surface an image of a remote process that is controlled in accordance with the determined parameters of the pose of the second object.

The step of actively generating may comprise the step of projecting a known image pattern to actively generate the image pattern on the surface of the first object, wherein the step of projecting is from either the second object if the step of actively generating is performed at the second object or a first location other than the second object and the first object if the step of detecting is performed at the second object.

The step of projecting may comprise projecting the image pattern from the second object. The step of detecting may comprise detecting the image pattern at the surface of the first object. The step of projecting may comprise projecting the image pattern from the first location. The step of detecting further comprises detecting the image pattern from a second location other than the first object and the second object.

The method may further comprise the step of maintaining the first object in a known pose during the steps of projecting and detecting. The method may further comprise the step of maintaining the second object in a known pose during the steps of projecting and detecting.

The surface of the first object may be substantially planar. The method may further comprise the step of detecting movement of the detected pattern, and the step of determining parameters of the pose of the second object comprises determining movement of parameters of the pose of the second object from the detected movement of the detected pattern.

The method may further comprise the step of detecting linear movement of the second object parallel to the surface by detecting motion against texturing on the surface.

The step of projecting may further comprise projecting the image pattern such that the image pattern is asymmetrical about an axis of rotation inline with a direction of projection of the image pattern. The step of projecting may further comprise projecting the image pattern such that the size of the image pattern varies continuously with distance from the first object inline with a direction of projection of the image pattern.

The step of actively generating the image pattern may include actively generating elements of the image pattern over time, and the step of detecting includes detecting elements of the formed image pattern in synchronization with actively generating the image elements.

The method of claim 1 wherein the steps of actively generating and detecting comprise actively generating on the surface which surface forms a three dimensional cavity with access for the second object through an opening in the first object, and detecting the image pattern formed on such surface, respectively.

The surface may comprise a plurality of substantially planar sub-surfaces. The step of projecting further comprises projecting the image pattern as a combination of three or more spot beams of known relationship. The step of actively generating may further comprise actively generating the image pattern as a combination of three or more spot beams of known relationship.

The step of projecting may comprise projecting the image pattern with image pattern elements directed at a plurality of angles about an axis of the second object. The method may further comprise the step of user imparting movement of the second object.

The step of projecting may further comprise projecting encoded information, other than pose-related information, in an image pattern projected from the second object.

The step of determining an element of the pose of the second object may further comprise determining a distance from the image pattern on the surface of the first object to a reference point on the second object based upon the size of the detected image pattern.

In a second aspect the invention provides a method of controlling instruments of a surgical robot in use on a heart, the method comprising the steps of receiving a signal that a heart is about contract, and initiating movement of the surgical robot instruments so as to accommodate movement of the heart in the vicinity of the instruments during contraction as movement of the heart occurs.

The step of receiving may further comprise receiving a signal related to an anticipated nature of the contraction, and the step of initiating further comprises utilizing the anticipated nature of the contraction from the signal to control the accommodation. The method may comprise the steps of detecting a contour of movement of a heart by, projecting an image pattern on to a surface of the heart in the vicinity of the instrument, repeatedly detecting the image pattern formed on the surface of the heart, and determining movement of the heart based on a transformation of the detected image pattern from reference image pattern data, and moving the surgical robot instruments so as to accommodate the contour of movement of the heart in the vicinity of the instrument, so that operator intended motions can be carried out from this normalized position.

In a third aspect the invention provides a method of controlling an instrument of a surgical robot comprising the steps of detecting a contour of movement of a heart by, projecting an image pattern on to a surface of the heart in the vicinity of the instrument, repeatedly detecting the image pattern formed on the surface of the heart, and determining movement of the heart based on a transformation of the detected image pattern from reference image pattern data, and moving the surgical robot instruments so as to accommodate the contour of movement of the heart in the vicinity of the instrument, so that operator intended motions can be carried out from this normalized position.

In a fourth aspect the invention provides a robot system comprising a robot including and controlling an instrument, controls for an operator to control the robot to operate the instrument, a controller for determining quantified information related to motion of the instrument, and a display for displaying the information from the controller to an operator of the robot during use of the robot.

In a fifth aspect the invention provides a method of conveying information regarding the latency between motion of a controller and motion of an instrument in a remote process controlled by the controller, the method comprising displaying to an operator of the controller an image of the instrument and at least a portion of the remote process surrounding the instrument in a direction of motion of the instrument, and overlaying on the displayed image, an image of the instrument in a pose requested by motion of the controller, such that the operator can see an image of the actual pose of the instrument, and the requested pose of the instrument.

In a sixth aspect the invention provides a method of conveying information regarding the latency between motion of a controller of a surgical robot and motion of an instrument of the surgical robot controlled by the controller, the method comprising displaying on a display visible to an operator of the controller, an image of the instrument and at least a portion of a surgical field surrounding the instrument in a direction of motion of the instrument, and overlaying on the displayed image, an image of the instrument in a pose requested by motion of the controller, such that the operator can see an image of the actual pose of the instrument, and the requested pose of the instrument.

In a seventh aspect the invention provides a method of controlling latency between motion of a controller and motion of the instrument in a remote process controlled by the controller, the method comprising the steps of acquiring an original image of the instrument and at least a portion of a surgical field surrounding the instrument in a direction of motion of the instrument, and displaying the original image to an operator of the controller, acquiring an instruction from the controller to move the instrument to an instructed pose relative to the original image, transmitting the instruction and information to identify the original image to the remote process, acquiring an updated image of the remote process, performing pattern recognition at the remote process on the image identified by the transmitted information and the updated image to determine a desired pose of the instrument relative to the updated image that corresponds to the instructed pose on the original image, and moving the instrument to the desired pose.

In an eighth aspect the invention provides a method comprising the steps of actively displaying on a surface of a first object an image of a remote process that is controlled in accordance with parameters of the pose of a second object spaced away from the first object, detecting an image pattern on the surface of the first object, wherein either the image pattern is actively generated from the second object or the image pattern is detected at the second object, determining parameters of the relative poses of the second object and the surface utilizing the detected image pattern and utilizing reference data for the image pattern, and controlling the remote process in accordance with the determined parameters of the pose of the second object.

In a ninth aspect the invention provides a method comprising the steps of projecting a known image pattern on to a surface of a first object, wherein the step of projecting is from either a second object or a first location other than the second object and the first object, and the first object, second object and first location are at a distance from one another, detecting the image pattern formed on the surface of the first object, wherein if the step of projecting is from the second object then the step of detecting is from either the first object, second object or a second location other than the first and the second object, and if the step of projecting is from the first location then the step of detecting is from the second object, and determining parameters of the pose of the second object utilizing the detected image pattern and reference image pattern data for the known pattern.

In a tenth aspect the invention provides a method of controlling an instrument of a robot comprising the steps of detecting a contour of movement of an object being worked by the instrument, projecting an image pattern on to a surface of the object in the vicinity of the instrument, repeatedly detecting the image pattern formed on the surface of the object, and determining movement of the object based on a transformation of the detected image pattern from reference image pattern data, and moving the robot instruments so as to accommodate the contour of movement of the object in the vicinity of the instrument, so that operator intended motions can be carried out from this normalized position.

In a eleventh aspect the invention provides an input interface comprising a pattern generator for actively generating an image pattern on a surface of a first object, a detector for detecting the image pattern on the surface of the first object, wherein the pattern generator or the detector is at a second object spaced away from the first object, and a computer for determining parameters of the relative poses of the second object and the surface utilizing the detected image pattern from the detector and utilizing reference data for actively generating the image pattern.

In a twelfth aspect the invention provides a system comprising a surgical robot including an instrument controlled by the robot, a computer for receiving a signal that a heart being operated on by the instrument is about to contract, and generating instructions to the robot to initiate movement of the surgical robot instrument so as to accommodate movement of the heart in the vicinity of the instruments during contraction as movement of the heart occurs.

In a thirteenth aspect the invention provides a robot system comprising a robot including and controlling an instrument, controls for an operator to control the robot to operate the instrument, a controller for determining quantified information related to motion of the instrument, and a display for displaying the information from the controller to an operator of the robot during use of the robot.

In a fourteenth aspect the invention provides a system for conveying information regarding the latency between motion of a controller and motion of an instrument in a remote process controlled by the controller, the system comprising a computer and a display for displaying to an operator of the controller an image of the instrument and at least a portion of the remote process surrounding the instrument in a direction of motion of the instrument, and an overlay on the displayed image, an image of the instrument in a pose requested by motion of the controller, such that the operator can see an image of the actual pose of the instrument, and the requested pose of the instrument.

In a fifteenth aspect the invention provides system for conveying information regarding the latency between motion of a controller of a surgical robot and motion of an instrument of the surgical robot controlled by the controller, the system comprising a computer and a display for displaying on a display visible to an operator of the controller, an image of the instrument and at least a portion of a surgical field surrounding the instrument in a direction of motion of the instrument, and overlaying on the displayed image, an image of the instrument in a pose requested by motion of the controller, such that the operator can see an image of the actual pose of the instrument, and the requested pose of the instrument.

In a sixteenth aspect the invention provides a system for controlling latency between motion of a controller and motion of the instrument in a remote process controlled by the controller, the system comprising a camera for acquiring an original image of the instrument and at least a portion of a surgical field surrounding the instrument in a direction of motion of the instrument, and a display for displaying the original image to an operator of the controller, acquiring an instruction from the controller to move the instrument to an instructed pose relative to the original image, and transmitting the instruction and information to identify the original image to the remote process, wherein the camera is also for acquiring an updated image of the remote process, a computer for performing pattern recognition at the remote process on the image identified by the transmitted information and the updated image to determine a desired pose of the instrument relative to the updated image that corresponds to the instructed pose on the original image, and instructing the remote process to move the instrument to the desired pose.

In a seventeenth aspect, the invention provides a computer readable medium storing program instructions executable by one or more processors in one or more computers for causing the computers to implement the method of any one of the method aspects.

Other aspects of the present invention and detailed additional features of the above aspects will be evident based upon the detailed description, FIGS. and claims herein, including for example systems corresponding to the methods of the above aspects, methods corresponding to the systems of the above aspects, input interfaces, wands, robots, computing systems, alignment systems, software, methods of using the above, and the like.

BRIEF DESCRIPTION OF THE DRAWINGS

For a better understanding of the present invention and to show more clearly how it may be carried into effect, reference will now be made, by way of example, to the accompanying drawings that show the preferred embodiment of the present invention and in which:

FIG. 3 is a perspective view of additional portions of an input interface, utilizing, for example, the input interface of FIG. 1, and including transmission means from the sensor array to computer, and a three dimensional viewer including superimposed force feedback information on top of a three dimensional image of a work space in accordance with various example embodiments of aspects of the present invention.

FIG. 4 and FIG. 5 are perspective views of details of two examples of force feedback information for the input interface of FIG. 3.

FIG. 6 is a perspective view and block view of various elements of a robotic control system, including the input interface of FIG. 1, in accordance with various embodiments of aspects of the present invention.

FIG. 6a1 is a perspective view of a further alternative user interface, similar to that illustrated in FIG. 6a, except that the sensor array is comprised of two panels, at an angle relative to each other, known to a computer.

FIG. 6a2 is a perspective view of another alternative user interface, similar to that illustrated in FIG. 6a, except that the camera is located in a stationary position above the surface.

FIG. 7 is a cross-sectional, perspective view of an example embodiment of a wand, including rechargeable battery and controller/encoder, various example controls, and light emitter cluster, which houses the light emitters.

FIG. 8 is a cross-sectional, perspective view of a faux forceps wand.

FIG. 8a is a cross-sectional, perspective view of an example embodiment of a wand similar to FIG. 7, but instead of multiple fixed emitters, there is one emitter, the beam of which is redirected by a mirror or other beam redirecting device.

FIG. 8b is a cross-sectional, perspective view of the distal end of the wand of FIG. 8a, illustrating an emitter beam which is redirected by a mirror.

FIG. 9 is a cross-sectional, perspective view of an example embodiment of a faux forceps wand which includes a finger slider and sensor and/or haptic feedback device.

FIG. 10 is a perspective view of a further example embodiment of an operator viewer, with force feedback information as illustrated in detail, and tool icons of available tools a selected tool.

FIG. 11 is a cross-sectional, perspective view which illustrates an example of relative movement of wand controls and consequent movement of a tool.

FIG. 17 is a cross-sectional, perspective view of a camera tool which illustrates the effect of spacing of neighboring projected dots on a surface at two stages of movement. The separations, along with known information: the angles of the beams, relative to the tool and the position of a camera tool provide a computer with a description of the changing position of the surface at each point in time.

FIG. 18 is a perspective view of a distal end of the camera tool of FIG. 17 projecting beams at various predetermined angles, relative to the tool.

FIGS. 29a to 29e are partial, sectional, perspective views of the operating theatre and remote work site, which illustrate methods to reduce or eliminate operational latency of the system.

DETAILED DESCRIPTION

Figure 1:
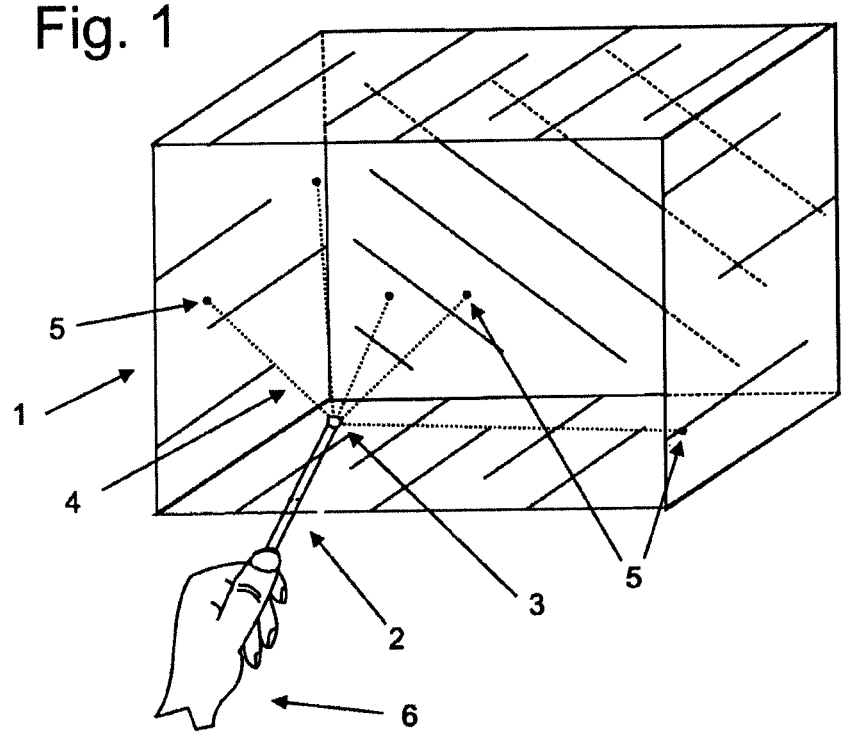
FIG. 1 is a perspective view of portions of an input interface including a first object, an open sided box having a surface (light sensor array), and a second object (a wand) projecting an image pattern (light beams) to actively generate an image pattern on the surface (spots of light) which is detected by the light sensor in accordance with various example embodiments of aspects of the present invention.

An object location, sometimes referred to as position, and orientation, sometimes referred to as attitude, will together be called the "pose" of the object, where it is understood that the orientation of a point is arbitrary and that the orientation of a line or a plane or other special geometrical objects may be specified with only two, rather than the usual three, orientation parameters.

A pose can have many spatial parameters, referred to herein as parameters. As described above, such parameters may include the location and orientation of the object. Parameters may include location information in one, two or three dimensions. Pose location parameters may also be described in terms of vectors, providing a direction and a distance. Pose orientation parameters may be defined in terms of an axis of the object, for example, the skew (rotation about the axis), rotation (rotation of the axis about an intersection of the axis and a line normal to a plane), and tilt (rotation of the axis about an intersection of the axis and a line parallel to the plane). Other pose orientation parameters are sometimes referred to as roll, pitch and yaw.

It will be evident to those skilled in the art that there are many possible parameters to a pose, and many possible methods of deriving pose information. Some parameters will contain redundant information between parameters of the pose. The principles described herein include all manner of deriving pose information from the geometric configuration of detector and surface described herein, and are not limited to the specific pose parameters described herein.

Pose parameters may be relative to an object (such as a surface), or some other reference. Pose parameters may be indirectly derived, for example a pose relative to a first object may be derived from a pose relative to a second object and a known relationship between the first object and second object. Pose parameters may be relative in time, for example a change in the pose of an object resulting from motion over time may itself by a pose element without determining the original pose element.

The description provided herein is made with respect to exemplary embodiments. For brevity, some features and functions will be described with respect to some embodiments while other features and functions will be described with respect to other embodiments. All features and functions may be exchanged between embodiments as the context permits, and the use of individual features and functions is not limited by the description to the specific embodiments with which the features and functions are described herein. Similarly, the description of certain features and functions with respect to a given embodiment does not limit that embodiment to requiring each of the specific features and functions described with respect to that embodiment.

In this description one or more computers are referenced. It is to be understood that such computers comprise some form of processor and memory, which may or may not be integrated in a single integrated circuit. The processor may be provided by multiple CPUs which may be integrated on a single integrated circuit as is becoming more and more common, or a single CPU. Dedicated processors may be utilized for specific types of processing, for example, those that are mathematically computationally intensive. The functions of the computer may be performed in a single computer or may be distributed on multiple computers connected directly, through a local area network (LAN) or across a wide area network (WAN) such as the Internet. Distributed computers may be in a single location or in multiple locations. Distributed computers may be located close to external devices that utilize their output or provide their input in order to reduce transmission times for large amounts of data, for example image data may be processed in a computer at the location where such data is produced, rather than transmitting entire image files, lesser amounts of post-processed data may be transmitted where it is required.

The processing may be executed in accordance with computer software (computer program instructions) located in the memory to perform the various functions described herein, including for example various calculations and the reception and transmission of inputs and outputs of the processor. Such software is stored in memory for use by the processor. Typically the memory that is directly accessible to the processor will be read only memory (ROM) or random access memory (RAM) or some other form of fast access memory. Such software, or portions thereof, may also be stored in longer term memory for transfer to the fast access memory. Longer term storage may include for example a hard disk, CD-ROM in a CD-ROM drive, DVD in a DVD drive, or other computer readable medium.

The content of such software may take many forms while carrying out the features and functions described herein and variants thereof as will be evident to those skilled in the art based on the principles described herein.

Patterns include for example the spots emitted from the emitters described herein. Patterns also include other examples provided herein such as ellipses and other curves. It may also include asymmetrical patterns such as bar codes. Actively generating a pattern includes for example a pattern on a computer monitor (herein called a screen) or other display device. Actively generating a pattern may alternatively include projecting the pattern onto a surface. A detector includes for example a camera or a sensor array incorporating for example CCD devices, and the like. Reference pattern data may include for example the location and direction of emitters, or other projectors.

Objects as used herein are physical objects, and the term is to be construed generally unless the context requires otherwise. When projection or detection occurs at an object it is intended to include such projection or detection from objects fixedly connected to the initial object and the projector or detector is considered to be part of the initial object.

Referring to the FIGS., like items will be referenced with the same reference numerals from FIG. to FIG., and the description of previously introduced items will not be repeated, except to the extent required to understand the principle being discussed. Further, similar, although not identical, items may be referenced with the same initial reference numeral and a distinguishing alphabetic suffix, possibly followed by a numerical suffix.

In some aspects embodiments described herein provide a solid state operator interface which accurately reports the movements of the working end of an operator's faux instruments, which are then accurately reported to the working end of the robot's tools. In the case of a surgical robot, the operator (surgeon) manipulates instruments similar to those the surgeon would normally use, such as a tubular wand, for a scalpel and an instrument that would be similar in shape to forceps. This approach reduces the training that is required to become adept at using a robotic system, and also avoids the deterioration of learned skills learned in the hands-on operating procedures.

In some aspects embodiments described herein provide an operator interface that permits an input device, and the hands of the operator, to move in a larger space, which would eliminate or reduce the occasions in which the system requires resetting a center point of operator interface movements.

In some aspects embodiments described herein provide an interface which allows for fine coordinated movements by input device, and by both hands, such as when the surgeon attaches a donor and recipient vessels with sutures.

In some aspects embodiments described herein provide an interface that may include haptic feedback.

In some aspects embodiments described herein provide an interface system that can position the tools at any point in time so that non-operationally created motions are fully compensated for, and a relatively small patch of surface, where the procedure is being carried out, is rendered virtually static to the operator's point of view.

In some aspects, embodiments described herein provide a method for virtually limiting latency, during the operation. In some other aspects, embodiments described herein provide a method for alerting an operator to the existence and extent of latency during the operation.

Referring to FIG. 1, an operator's hand 6 controls the motion of the wand 2 within a sensor array 1, comprised of five rectangular segments forming an open-sided box. Narrow light beams 4 emanate from a light-emitting cluster 3 and project spots of light 5 on the light sensors of the sensor array 1.

Figure 2:
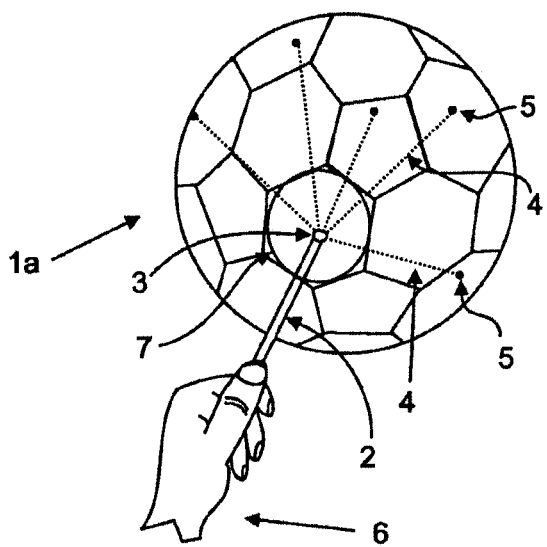
FIG. 2 is a perspective view of portions of an alternative input interface including a buckyball shaped sensor array in accordance with various example embodiments of aspects of the present invention.

Referring to FIG. 2, the box sensor array 1 of FIG. 1 is replaced by a buckyball-shaped sensor array 1a, comprised of hexagonal and pentagonal segments, and an opening 7, which permits the wand 2 to be inserted into the sensor array 1a.

Referring to FIG. 3, a system, includes the sensor array 1 and transmission means 11a that deliver signals from the segments of the sensor array 1 at interface pads 11b to computer 11. A three dimensional viewer 8 includes superimposed force feedback information 10b, 10c, as shown in detail 10a on top of the three dimensional image of the work space.

Referring to FIG. 4 and FIG. 5, two examples are shown of the force feedback information 10d, 10e, 10f and 10g, which may be used in substitution or in addition to haptic feedback.

Referring to FIG. 6, various elements of a robotic control system are shown. FIG. 6 illustrates an example where a body 14 is being operated on through an incision 14a. The robot in this case is fitted with a tool controller 15 and example tools: forceps 15b, three dimensional camera 15c and cauterizing scalpel 15d. The robot's principal actuators 15a control the various movements of the tools in response to the positions of the wands 2 including the goose-neck camera guiding wand 13, and commands of the operator.

Figure 6A:
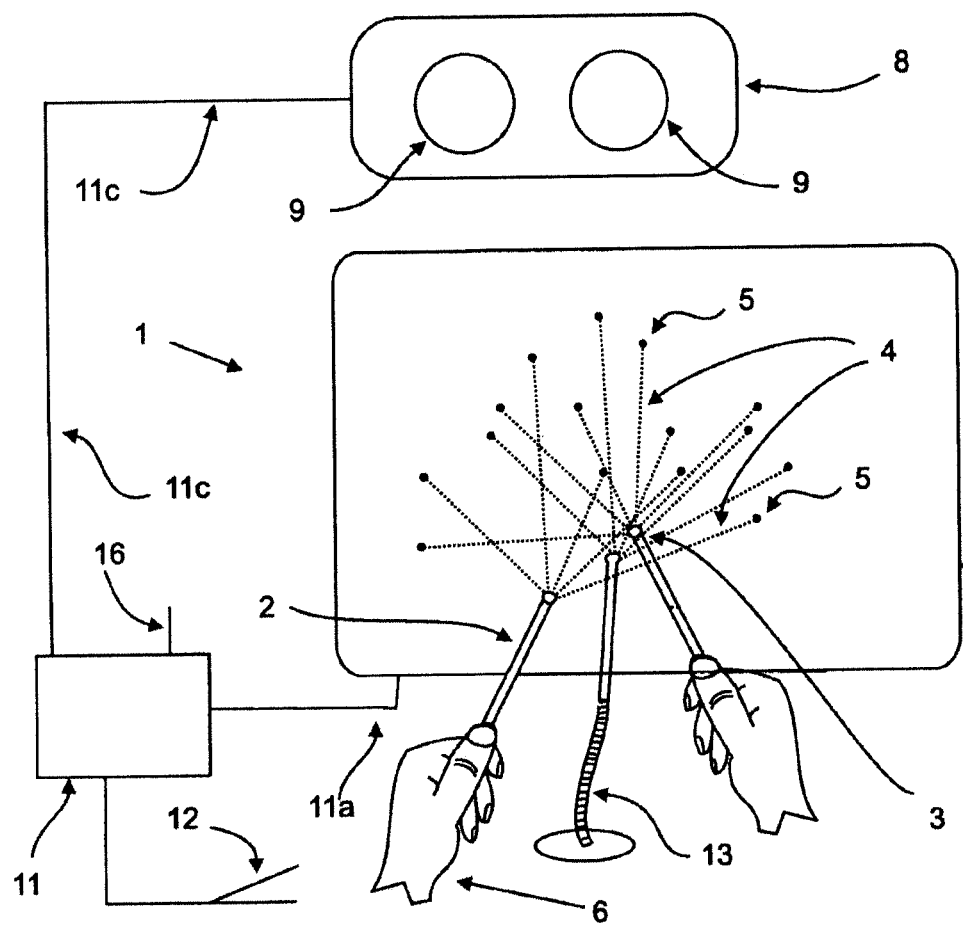
FIG. 6a is an example of an alternative input interface which uses only a single panel to form the sensor array.

Referring to FIG. 6a, an example of a user interface using a single panel to form the sensor array 1 is shown.

Referring to FIG. 6a1, a user interface is shown that is similar to that illustrated in FIG. 6a, except that the sensor array 1b is comprised of two panels at an angle relative to each other, which is known to the computer 11.

Referring to FIG. 6a2, an interface is shown that is similar to that illustrated in FIG. 6a, except that the camera 3c is located in a stationary position above the surface 1b, such that it can view the spots of light 5 projected onto the surface and their position on the surface, but at an angle which minimizes or eliminates interference by the wand 2 with the emitted beams 4. The camera 3c is connected to the computer 11 by connecting means 3b1.

Figure 6B:
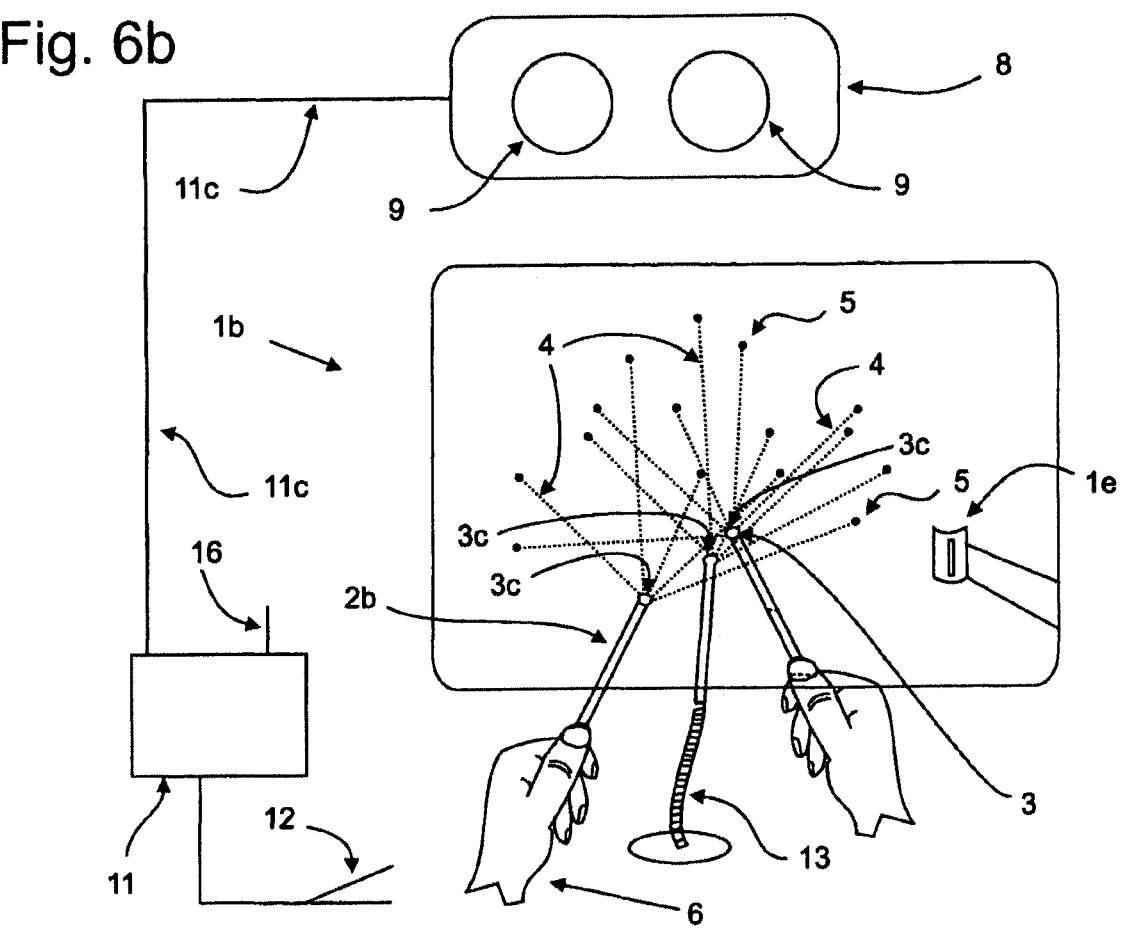
FIG. 6b is a block diagram illustrating another further alternate user interface in which a lens is included and which tracks the spots projected onto a surface and transmits the information wirelessly to the controller/encoder and/or the computer.

Referring to FIG. 6b, a user interface is shown in which a lens 3c is included and which tracks the spots of light 5 projected onto a surface 1b, which may not contain sensors, and transmits the information wirelessly to the controller/encoder 18 and/or the computer 11.

Figure 6C:
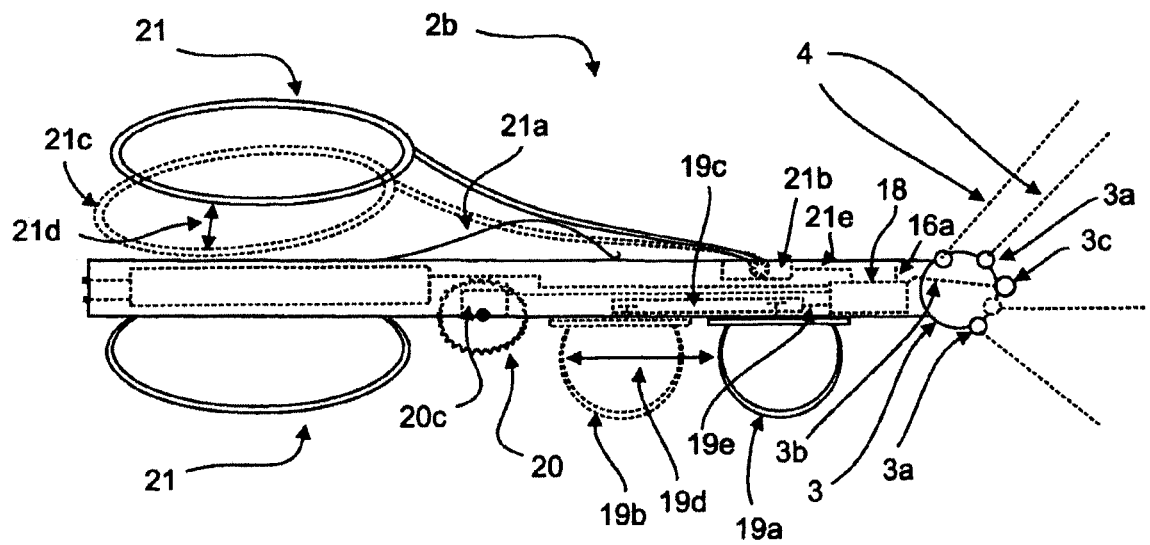
FIG. 6c is a cross-sectional, perspective view of an example embodiment of a faux instrument wand which includes a lens.

Referring to FIG. 6c, a faux forceps wand 2b is shown that includes a lens 3c.

Referring to FIG. 7, a generally cylindrical wand 2 is shown that includes a rechargeable battery 17 and a controller/encoder 18, various example controls 19, 20, 20a and a light emitter cluster 3, which houses light emitters 3a.

Referring to FIG. 8, the faux forceps wand 2b is shown that has finger holes 21, return spring 21a and sensor/haptic feedback controller 21b.

Referring to FIG. 8a, the wand 2 is shown similar to FIG. 7, but instead of multiple fixed emitters 3a, there is one emitter 3a, the beam 4 of which is redirected by a mirror 3d or other beam redirecting device. FIG. 8a also illustrates the wand 2 with a camera 3c.

Referring to FIG. 8b, shown is a cross-sectional, perspective view of the distal end of wand 2, illustrating in greater detail emitter 3a and beam 4, part of which is redirected by mirror 3d1, in some embodiments being one of an array of mirrors 3e.

Figure 8C:
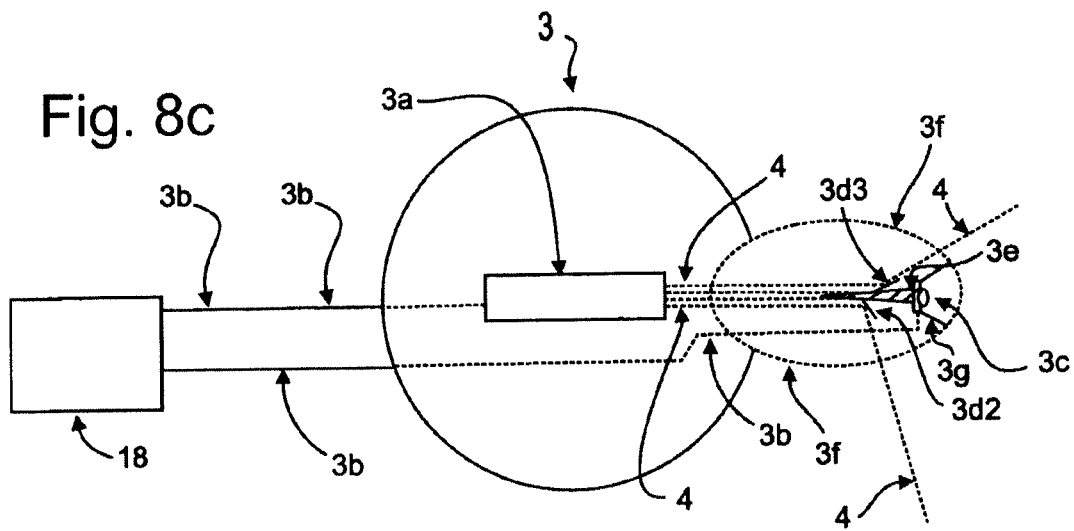
FIG. 8c is a cross-sectional, perspective view of the distal end of the wand of FIG. 8a, illustrating an emitter beam which is redirected by mirrors.

Referring to FIG. 8c, shown is a cross-sectional, perspective view of the distal end of wand 2, illustrating in greater detail the emitter 3a, beam 4, part of which is redirected by mirrors 3d2 and 3d3. FIG. 8c also illustrates an alternative location for camera 3c, in this case being located at the distal end of the mirror array 3e.

Figure 8D:
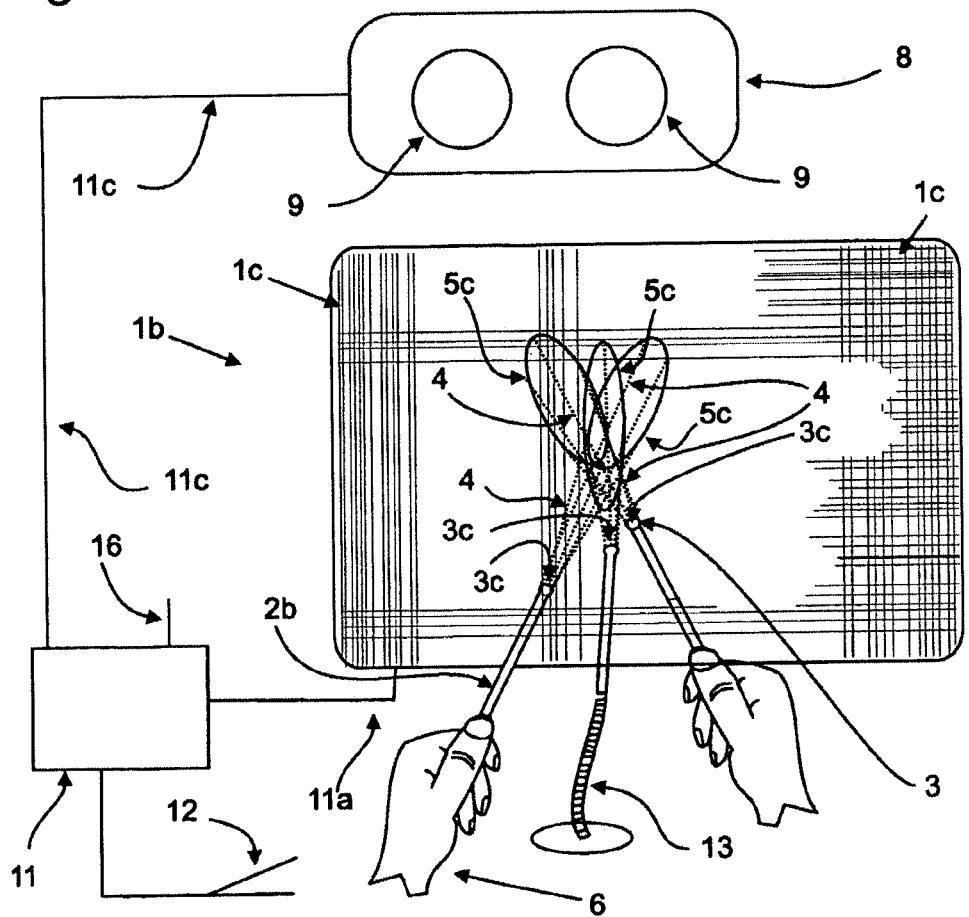
FIG. 8d is a perspective view of a surface on which an addressing grid has been overlain. For diagrammatical clarity, only parts of the grid have been illustrated, it being understood that the grid is continuous over the surface.

Referring to FIG. 8d, a surface 1b has an addressing grid 1c overlain. For diagrammatical clarity, only parts of the grid have been illustrated, it being understood that the grid 1c is continuous over the surface 1b.

Referring to FIG. 9, the faux forceps wand 2b includes a finger slider control 19a and sensor and/or haptic feedback device 19c.

Referring to FIG. 10, an operator viewer 8 has force feedback information 10 as illustrated in detail 10a, and also illustrated in FIG. 3. Tool icons 10h represent available tools. In this example, the operator has selected a forceps icon 26b for the left hand and a wrench tool icon 27b for the right hand. As an example, the respective selected tool is indicated by the icon being bolded.

Referring to FIG. 11, example relative movement of the wand 2b controls is shown, including the finger hole control 21, and the finger slider control 19a, (See FIG. 9), and the consequent movement of a tool 26 (See FIG. 11).

Figure 12:
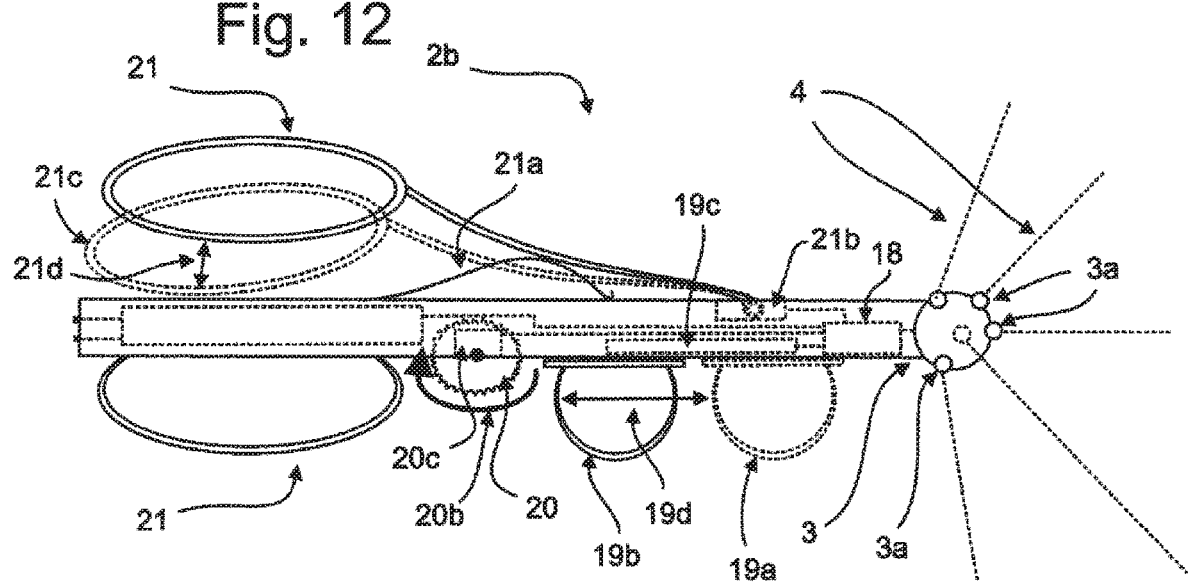
FIGS. 12, 13 and 14 are cross-sectional, perspective views which illustrate an example of relative movement of wand controls and consequent movement of a tool relative to a bolt.
Figure 13:
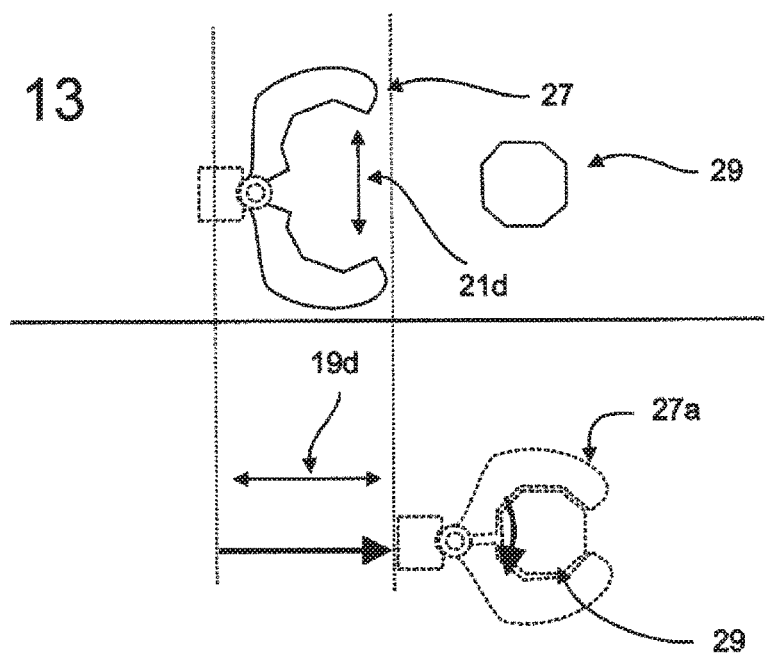
Figure 14:
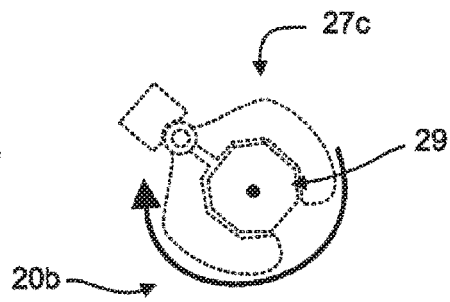

Referring to FIGS. 12, 13 and 14, example of relative movement of the wand 2b controls is shown, including a finger hole control 21, the finger slider control 19a, a rotary control 20 and the consequent movement of a tool 27 relative to a bolt 29.

Figure 15:
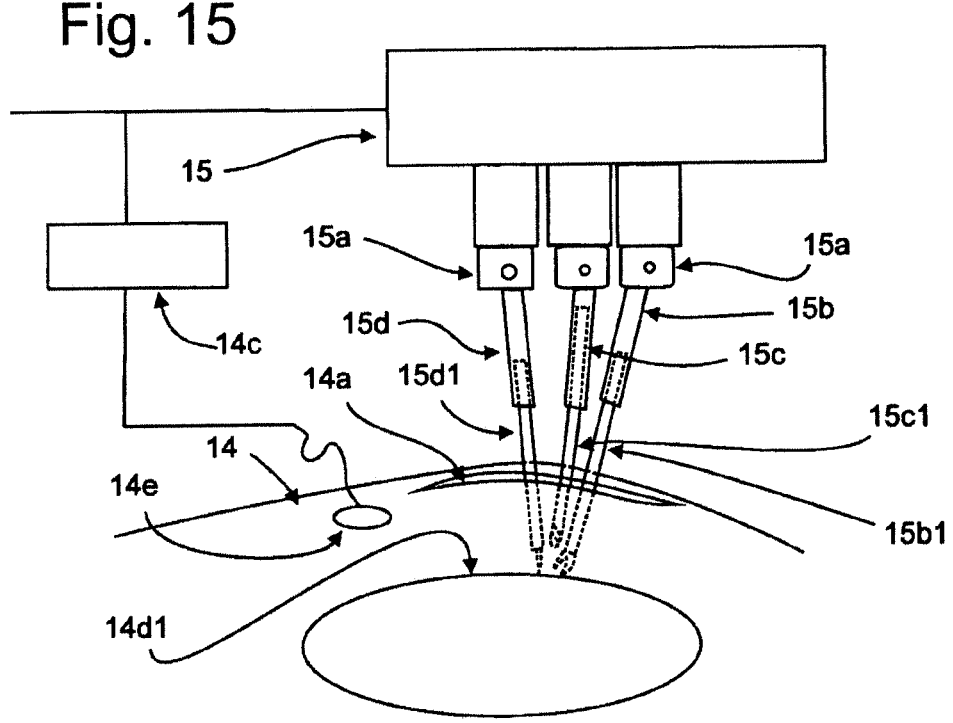
FIGS. 15 and 16 are cross-sectional, perspective views which illustrate an example of tools with adjustable extensions, which can retract in order to compensate for a rising and falling surface in accordance with an example embodiment of an aspect of the present invention.
Figure 16:
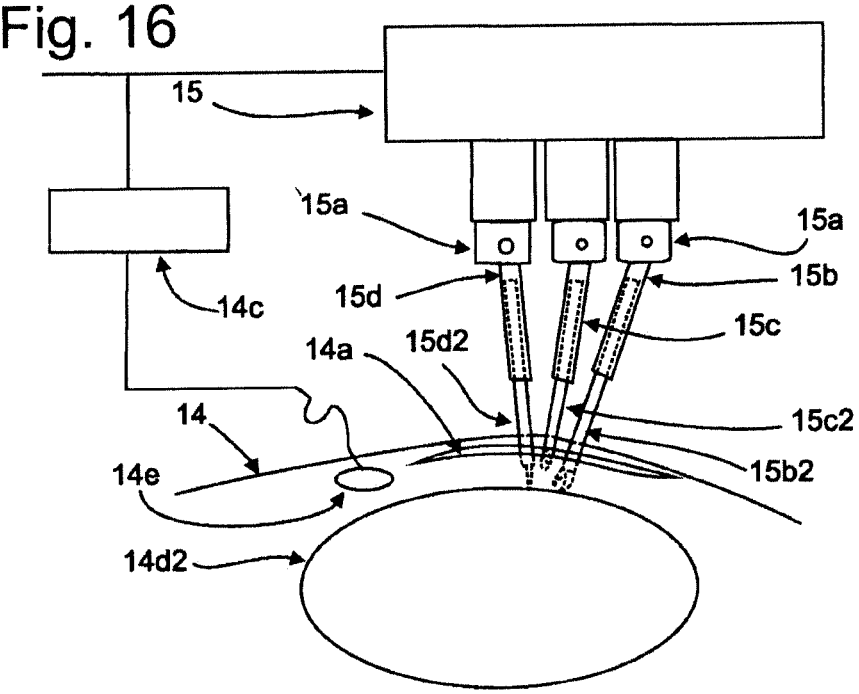

Referring to FIGS. 15 and 16, example tools 15b, 15c and 15d have respective adjustable extensions 15b1, 15c1 and 15d1 which can retract 15b2, 15c2 and 15d2 in order to compensate for rising and falling of a surface, for example a heart surface 14d1, 14d2.

Referring to FIG. 17, camera tool 15c views the effect of the spacing of neighboring projected dots/spots of lights 5 on the surface of the heart 14d1, 14d2, at two stages in the heart's beat. The separations, along with known information: the angles of the beams 4, relative to the tool 15c and the position of the camera tool 15*c*, provide computer 11 with a description of the changing position of the heart surface at each point in time. It also illustrates one example position of cameras, or camera lenses 3*c*1 and 3*c*2.

Referring to FIG. 18, distal end of the camera tool 15*c* is shown in detail. The emitter cluster 3 and emitters 3*a* project beams 4 at various predetermined angles, relative to the tool 15*c*.

Figure 19:
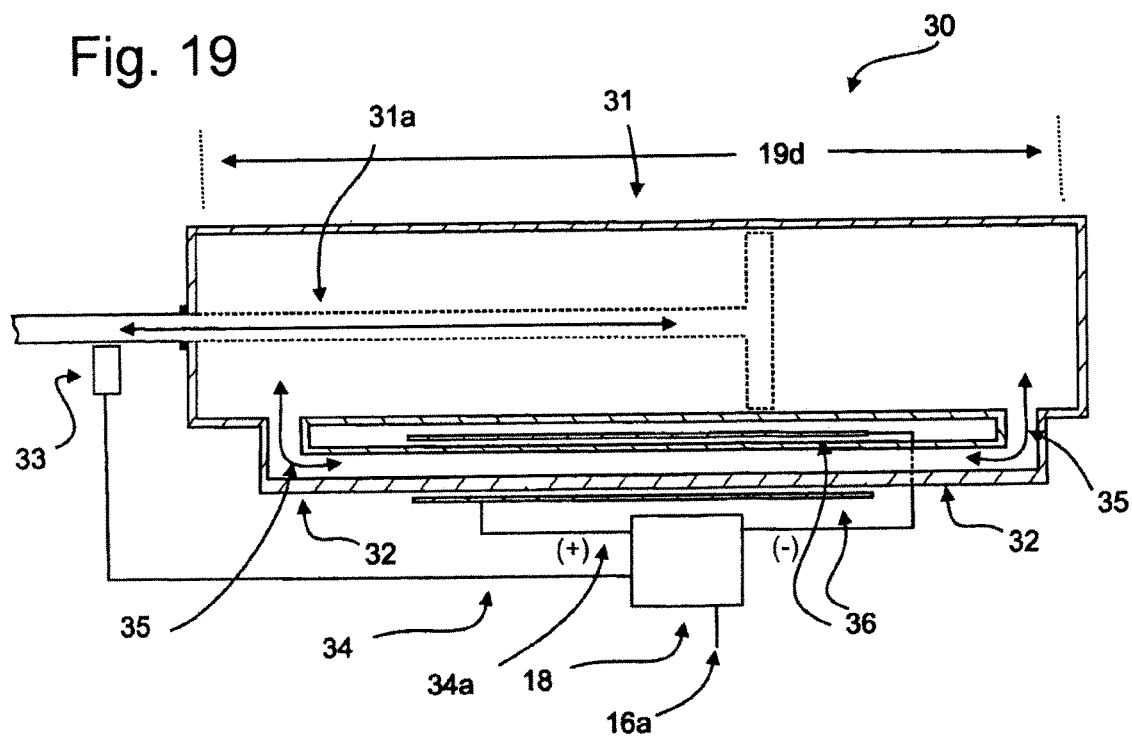
FIG. 19 is a cross-sectional, block diagram of an example passive haptic feedback device in which the flow of an electro-rheological or magneto-rheological fluid is controlled by an electrical or magnetic field between elements, which can be electrodes or magnetic coils in accordance with an embodiment of an aspect of the present invention.

Referring to FIG. 19, an example passive haptic feedback device has flow of an electrorheological or magnetorheological fluid controlled by an electrical or magnetic field between elements 36, which can be electrodes or magnetic coils. The control of the flow of this fluid affects the speed with which piston 31*a* can move back and forth through the cylinder 31.

Figure 20:
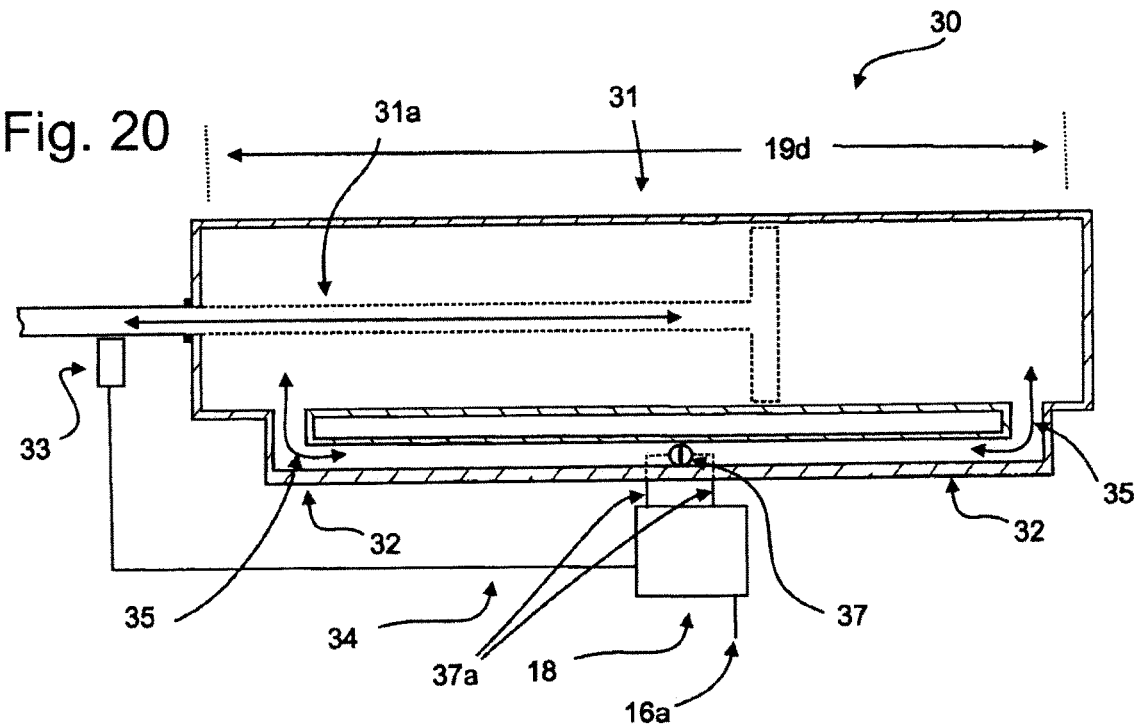
FIG. 20 is a cross-sectional, block view of an alternate embodiment of a passive haptic feedback device in which the flow of fluid, such as saline or glycerin is controlled by an electrical valve.

Referring to FIG. 20, the example passive haptic feedback device has a flow of fluid, such as saline or glycerin, controlled by an electrical valve 37. The control of the flow of this fluid affects the speed with which piston 31*a* can move back and forth through the cylinder 31.

Figure 21:
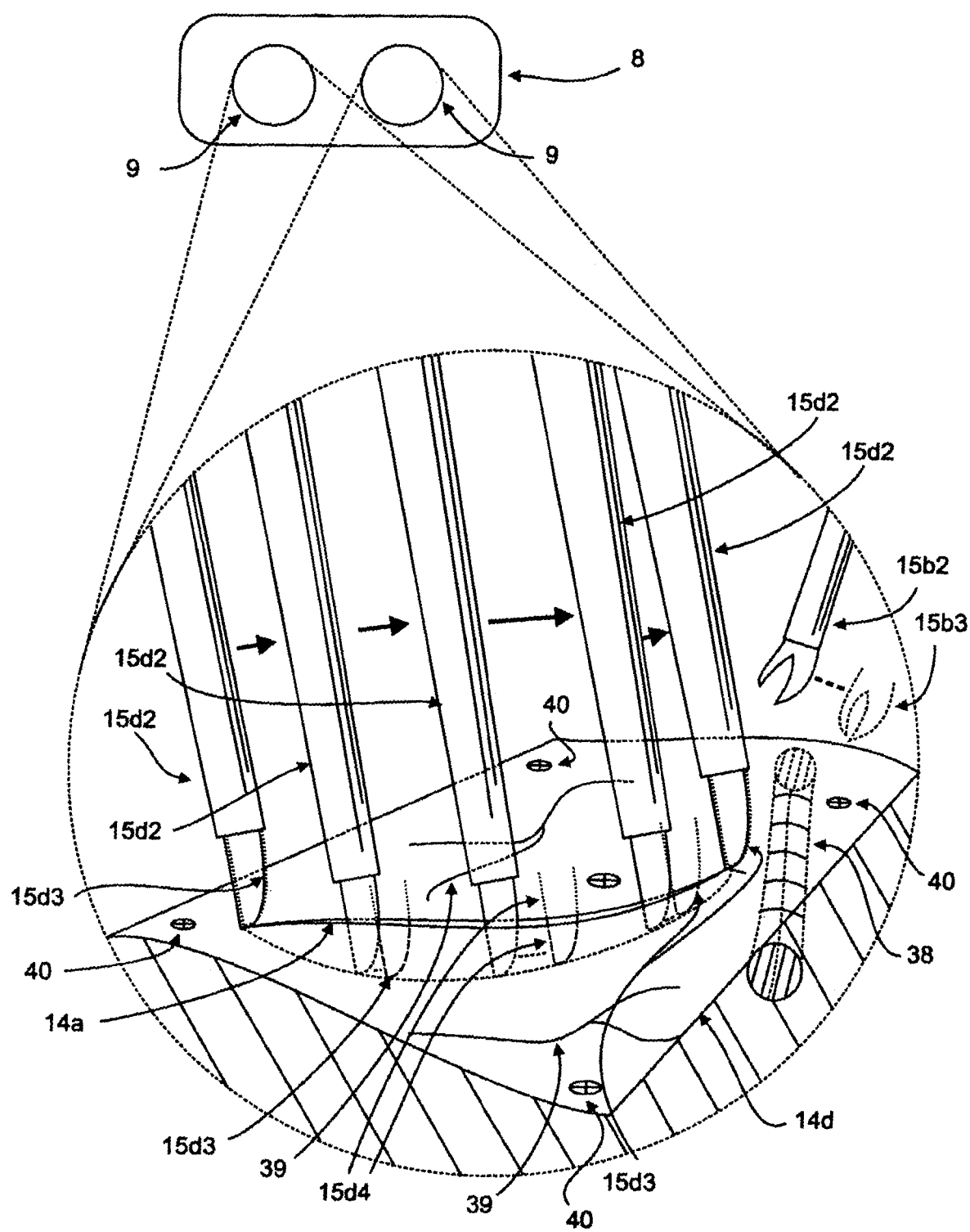
FIG. 21 is a cross-sectional, perspective view of the operator's view of a worksite as viewed through an example embodiment of a viewer with eyepieces, illustrating superimposed tool cursors of the operator's intended position of tools at the worksite, and the actual position of the tools at the worksite.

Referring to FIG. 21, an operator's view of the worksite (a remote process) seen through the viewer 8 and eyepieces 9 has superimposed tool cursors 15*d*3 and 15*b*3 that illustrate the operator's intended position of the tools at the worksite. Respective actual positions of the tools 15*d*2 and 15*b*2 at the worksite are also shown in the viewer 8 to display to the operator the difference between the two due to temporal latency.

Figure 22:
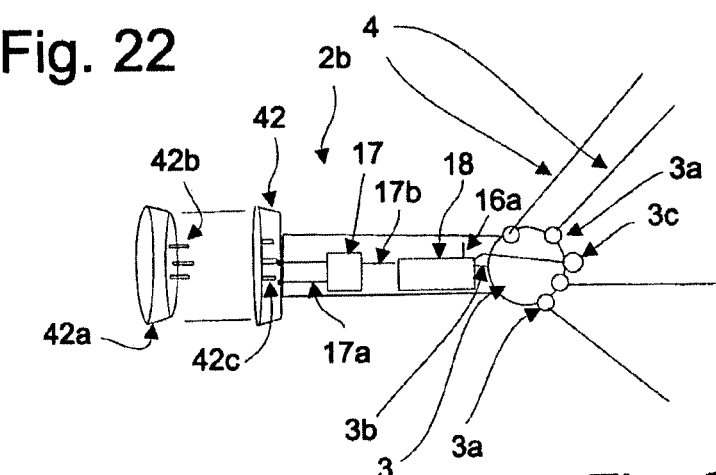
FIG. 22 is a cross-sectional, perspective view of an example wand attached to any body part, tool, or other object, by means of connectors, which have complementary indexing means, to ensure their proper alignment.

Referring to FIG. 22, the wand 2*b* may be attached to any body part, tool 15*d*2 15*c*2, or other object, by means of connectors 42 and 42*a*, that have complementary indexing means 42*c* and 42*b*, to ensure their proper alignment. Where an external camera 3*c*, such as illustrated in FIG. 6*a*2, or a sensor array 1, as illustrated in FIG. 23, is provided, the wand 2*b* may then not have an integral camera 3*c*.

Figure 23:
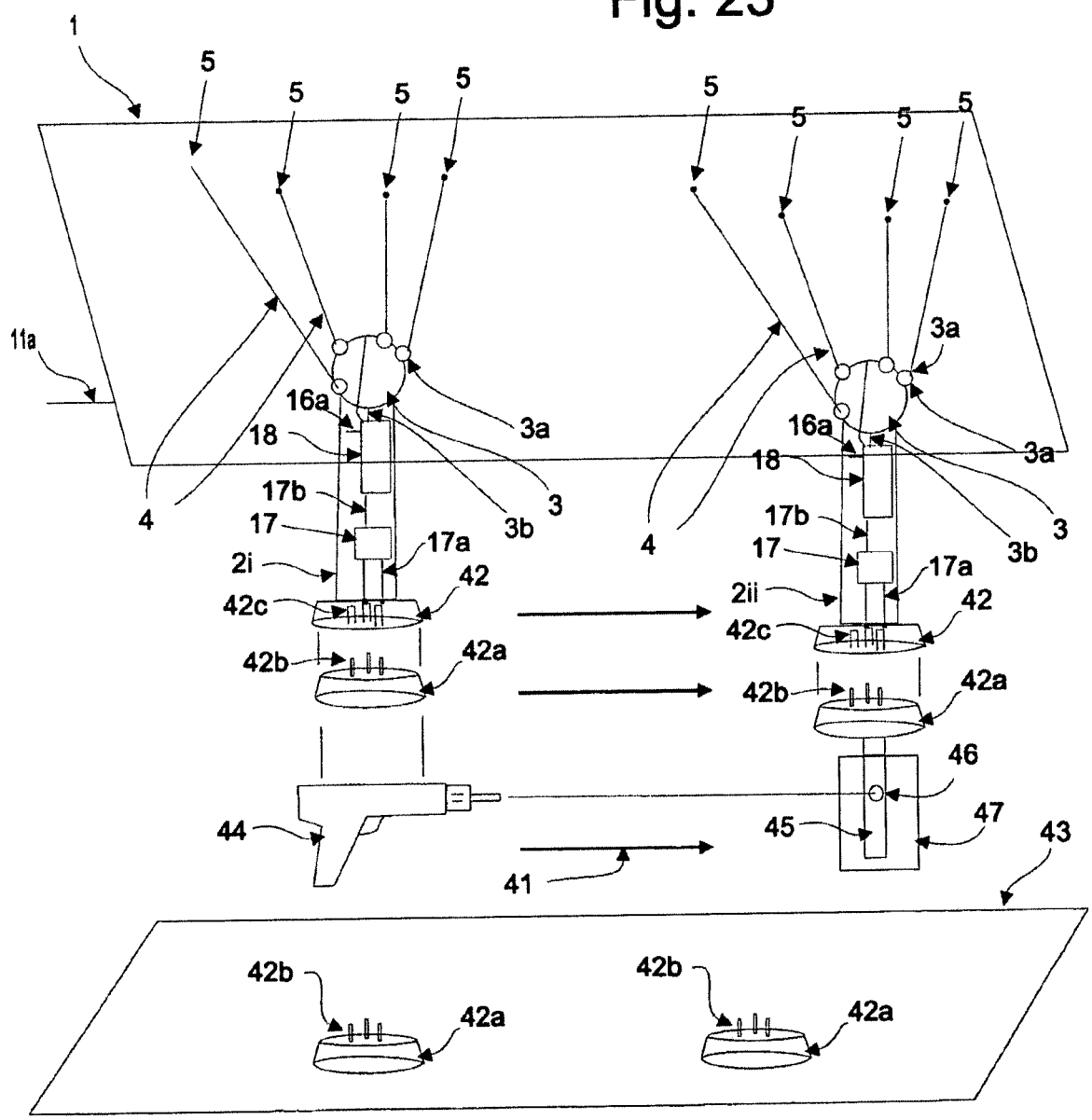
FIG. 23 is a cross-sectional, perspective view of two wands that can be aligned in a desired manner, or be placed in a desired orientation or position with respect to each other or another object. In this example a drill is positioned so that it can drill through a hidden hole.

Referring to FIG. 23, two wands 2*i* and 2*ii* (similar to wand 2*b* shown in FIG. 22) can be aligned in a desired manner, or be placed in a desired orientation or position with respect to each other or another object. In this example a drill 44 is positioned so that it can drill through a hidden hole 46.

Figure 24:
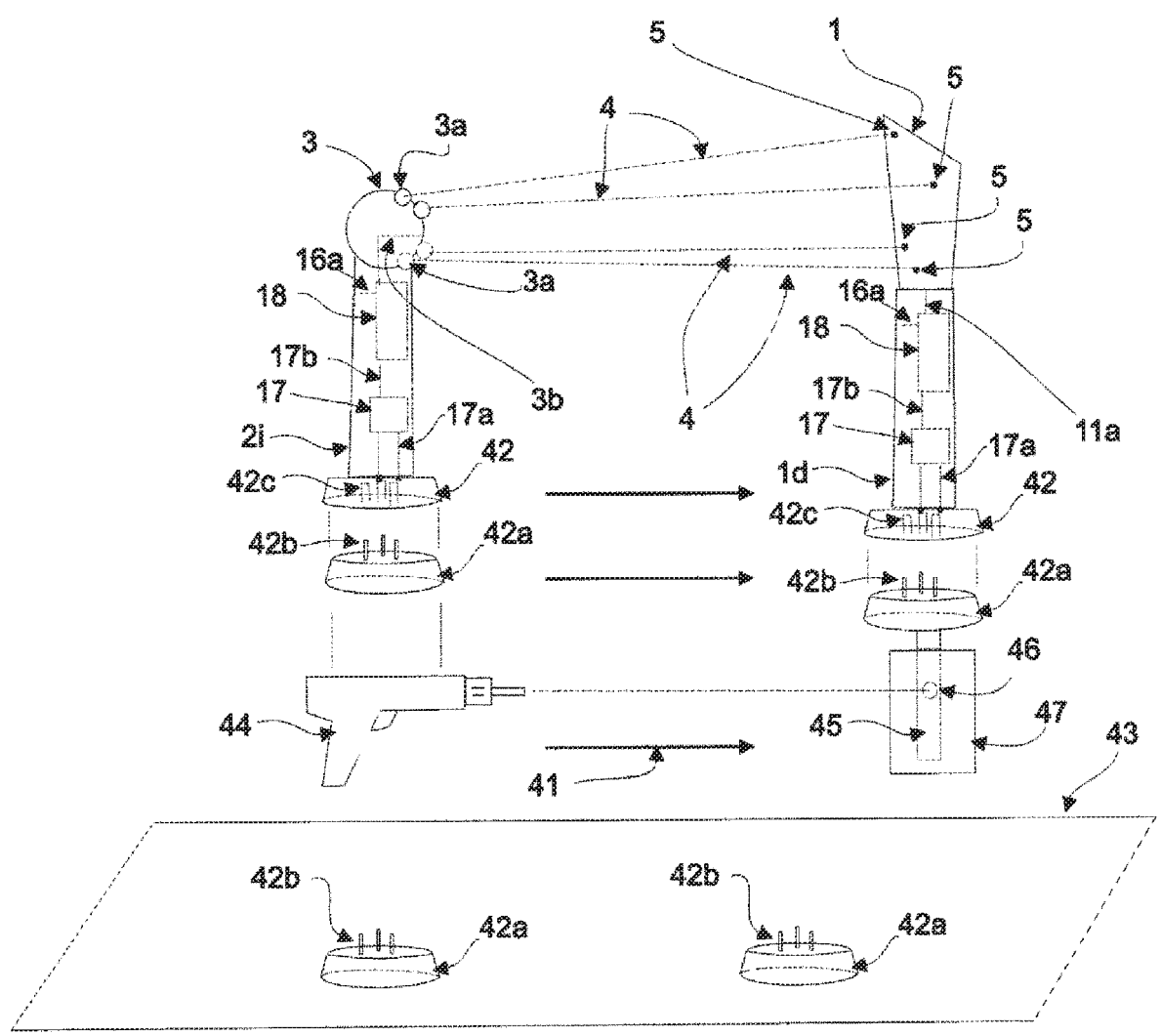
FIG. 24 is a cross-sectional, perspective view of one wand, and sensor array assembly (an example detector) which can be aligned in a desired manner, or be placed in a desired orientation or position with respect to each other or another object. In this example a drill is positioned so that it can drill through a hidden hole. A sensor array replaces the emitter housing in the sensor array assembly but the assembly is otherwise similar in construction to a wand. The sensor array communicates with a controller/encoder through communicating means and thence wirelessly to a computer.

Referring to FIG. 24, a sensor array assembly 1*d* replaces wand 2*ii* and the wand 2*i* and sensor array assembly 1*d* can be aligned in a desired manner, or be placed in a desired orientation or pose with respect to each other or another object. In this example the drill 44 is posed so that it can drill through the hidden hole 46. The sensor array 1 replaces the emitter housing 3 but is otherwise similar in construction to the wand 2. The sensor array 1 communicates with the controller/encoder 18 by communicating means 11*a* and thence wirelessly to computer 11 (not shown).

Some general elements of embodiments of some aspects of the present of invention will now be discussed.

One embodiment is a system which accurately records the motions of the working end of an operator's faux instruments, herein referred to as a wand, which can approximate the shape of the devices the operator would use in a manual procedure.

These motions are reported to the working end of the tools that the robot applies to the work site.

Other embodiments simply use the wand as an input device and its shape may not in any way relate to a particular instrument. For clarity, this disclosure will use a surgical interface to illuminate some convenient features of the invention, but for some embodiments the shape of the wand may not in any way mimic standard tools or instruments. It should also be noted that reference is made to a system controlling robotically controlled tools. It should be understood that some embodiments will control actuators that perform all types of work, such as controlling reaction devices, such as rocket motors or jet engines; the position of wing control surfaces, to name a few. The system may control virtual computer generated objects that are visually displayed or remain resident within the computer and where actuators may not even be used. Embodiments of this type would include manipulation of models of molecular structures (molecular modeling) and manipulation of protein structures. In such embodiments the wand may be thought of as a computer mouse in three dimensions, for example allowing the operator to view a three dimensional image of a structure, and then to make alterations to it, by moving the wand and making control commands, for example in the space in front of a sensor array. Such an embodiment of the wand and method could be used in architecture, machine design or movie animation. It will be recognized by those skilled in the art that these are examples only of uses of such embodiments and the embodiments are not limited to these examples.

In some described embodiments wands 2 incorporate light-emitting elements 3*a* that collectively cast multiple narrow beams of light, at known angles to each other, onto a sensor array 1 constructed of one or more light detecting panel(s) as illustrated on FIG. 3. The light detecting panel(s) reports the location of the incident light, in real-time, to a computer. Knowing the angles at which the emitters 3*a* project the light beams from the wand 2, the computer can convert various locations of incident spot of light 5 of the light beams 4, using triangulation and mathematical methods and algorithms, well known to the art, to calculate the position and attitude of the wand 2 relative to the sensor array 1, at each particular time interval. As the wand 2 moves, so do the spots of incident light 5 on the sensor array(s) 1, and so the computer can produce a running calculation of the position and attitude (example parameters of the pose) of the wand 2, from time to time. The computer can convert changes in parameters of the pose into instructions to the robot to assume relative motions. Small changes in the position and attitude of the wand can trace relatively large positional changes where the spots of light 5 fall on the sensor array 1. This can allow for accurate determining of the position and attitude of the wand.

In general there are four orientation problems:

A) Absolute Orientation Problem

To solve this problem one can determine, for example, the transformation between two coordinate systems or the position and orientation of a range sensors in an absolute coordinate system from the coordinates of calibration points. This can be done by recovery of a rigid body transformation between two coordinate systems. One application is to determine the relationship between a depth measuring device, such as a range camera or binocular stereo system, and the absolute coordinate system.

In the case of range camera, the input is at least a set of four conjugate pairs from one camera and absolute coordinates. In the case of a binocular stereo system, input is at least three conjugate pairs seen from the left and right camera.

B) Relative Orientation Problem

To solve this problem one can determine, for example, the relative position and orientation between two cameras from projections of calibration points in the scene. This is used to calibrate a pair of cameras for obtaining depth measurements with binoculars stereo.

Given n calibration points, there are 12+2n unknowns and 7+3n constraints.

At least 5 conjugate pairs are needed for a solution.

C) Exterior Orientation Problem

To solve this problem one can determine, for example, the position and orientation of a camera in an absolute coordinate system from the projections of calibration points in a scene. This problem must be solved for an image analysis application when necessary to relate image measurements to the geometry of the scene. This can be applied to a problem of position and orientation of a bundle of rays.

D) Interior Orientation Problem

To solve this problem one can determine, for example, the internal geometry of a camera, including camera constants, location of the principal point and corrections for lens distortions.

Some examples of these problems and their solutions are found in Ramesh Jain, Rangachar Kasturi and Brian G. Schunck, Machine Vision, McGraw-Hill, New York, 1995. ISBN 0-07-032018-7. Chapter 12 on Calibration deals in particular with an absolute orientation problem with scale change and binocular stereo, and with camera calibration problems and solutions which correlate the image pixels locations to points in space. Camera problem includes both exterior and interior problems.

In addition to calibration problems and solutions, the Jain et al reference addresses an example problem and solution for extracting distance or depth of various points in the scene relative to the position of a camera by direct and indirect methods. As an example, depth information can be obtained directly from intensity of a pair of images using two cameras displaced from each other by a known distance and known focal length. As an alternative example solution, two or more images taken from a moving camera can also be used to compute depth information. In addition to those direct methods 3D information can also be estimated indirectly from 2D intensity images known as "Shape from X Technique", where X denotes image cues such as shading, texture, focus or motion. Examples are discussed in Chapter 11 in particular.

The above Jain et al. reference is hereby incorporated by reference into the detailed description hereof.

Figure 26:
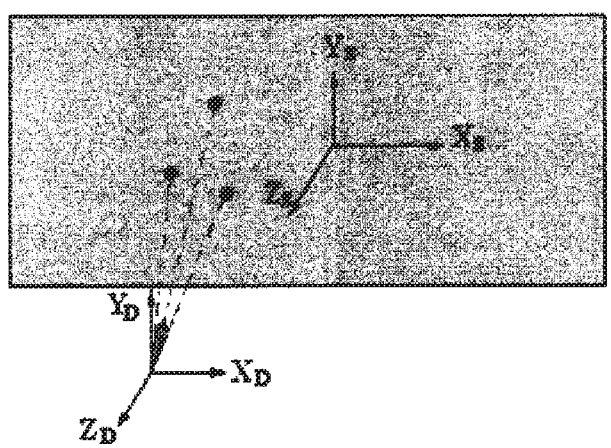
FIG. 26 is a graphic illustration of a screen plane (surface of a first object) and device planes' with mounted lasers (second object) and related coordinate systems.
Figure 27:
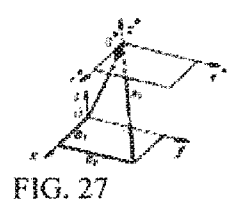
FIG. 27 is a graphic illustration of a linear translation between coordinate systems of FIG. 26.
Figure 28:
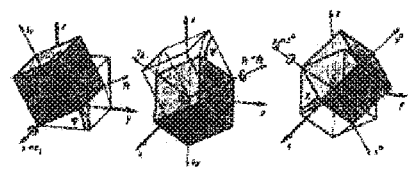
FIG. 28 is a graphic illustration of a rotational translation between coordinate systems of FIG. 26.

As a further example discussion of solutions to mathematical calculations that may be used to determine parameters of a pose of the wand for the purposes of determining 3D-position of a hand-held device equipped with laser pointers through a 2D-image analysis of laser point projections onto a screen, two sets of coordinate systems can be defined as shown in FIG. 26. The centre of a first coordinate system (xS,yS,zS) can be placed in the middle of the plane that coincides with the screen (projection) plane and is considered to be fixed. The lasers installed on the hand-held device can be described with a set of lines in a second coordinate system (xD,yD,zD) which origin agrees with an intersection of the laser pointers. Additionally, the second coordinate system can have a freedom of translation and rotation as shown in FIGS. 27 and 28. Translation and rotation coordinates such as those shown in FIGS. 27 and 28 can also be found in linear algebra book such as Howard Anton, John Wiley & Sons, 4th edition ISBN 0-471-09890-6; Section 4.10, at pp. 199 to 220.

The projection of the laser on the fixed plane is mathematically equivalent to finding the intersection between the plane equation zS=0 and the line equation describing the laser path. However, the line equations have to be transformed in the original coordinate system. There are many ways to define an arbitrary rotation and translation of one coordinate frame into another. One of the ways is via the transform matrix elements.

The table 1 and 2 shows the coordinate transforms of the point P from one coordinate system to the other as a result of the linear transposition and rotation.

TABLE 1

Linear translation $x = x^* + a1$
$y = y^* + a2$
$z = z^* + a3$

TABLE 2

Rotational transformation and definition of $a_{ik}$ coefficients

| $a_{ik}$ | | k = 1 | k = 2 | k = 3 |
|---|---|---|---|---|
| $x = a_{11}x^* + a_{12}y^* + a_{13}z^*$ | i = 1 | $\cos\psi\cos\chi$ | $\cos\psi\sin\chi$ | $\sin\psi$ |
| $x = a_{21}x^* + a_{22}y^* + a_{23}z^*$ | i = 2 | $\cos\varphi\sin\chi + \sin\varphi\sin\psi\cos\chi$ | $\cos\varphi\cos\chi - \sin\varphi\sin\psi\sin\chi$ | $-\sin\varphi\cos\psi$ |
| $x = a_{31}x^* + a_{32}y^* + a_{33}z^*$ | i = 3 | $\sin\varphi\sin\chi - \cos\varphi\sin\psi\cos\chi$ | $\sin\varphi\cos\chi + \cos\varphi\sin\psi\sin\chi$ | $\cos\varphi\cos\psi$ |

The table 3 is a summary of example laser property and image analysis requirements for the reconstruction of the translation or rotation of the hand held device based on the observations of movement of the projection point as set out above. For the purpose of this discussion, multiple lasers are equivalent to a single laser split into multiple spot beams.

| # of lasers | Translation | | | Rotation | | |
|---|---|---|---|---|---|---|
| | x | y | z | Along Z | Along x | Along y |
| 1 | ☑ | ☑ | Requires the light source with large dispersion angle. Requires edge detection and area or perimeter calculations. | Possible with the off set sensor and path reconstruction from minimum 3 frames for large angles. However, not very sensitive for small rotational angles. | Not detectable for the narrow laser beam. It would be interpreted as the translation. In the case of the dispersed beam, requires edge detection and shape reconstruction. | |
| 2 | ☑ | ☑ | ☑ Requires non parallel laser beams and distance calibration. | Problem with detection of left-right laser equivalent to 180° rotation. Requires marking of one of the lasers. Still requires path reconstruction via frame history. | It would be interpreted as the translation in the case of horizontal or vertical alignments. For misaligned lasers, not very sensitive and requires the distance calculation and calibration. | |

| # of lasers | Translation | | | Rotation | | |
|---|---|---|---|---|---|---|
| | x | y | Z | Along Z | Along x | Along y |
| 3 | ☑ | ☑ | ☑ With non parallel laser beams. | Requires marking of one of the lasers. | Requires area or perimeter calibration/calculation. | |
| 4 or more | Can provide additional information to potentially avoid singularities or ambiguities. | | | | | |

Additional image frames can be used to change the number of lasers, or spots used at any one time. The linear transposition in x and y direction can be reconstructed from the center of mass. The translation along the z axis can utilize a calibration of the area/perimeter of the triangle. Detection of the rotation around z-axis can be achieved with marking of one of the lasers or by asymmetrical placement of lasers. Whereby, the marking of the laser may result in the faster processing time compared to the second option which requires the additional image processing in order to find the relative position of triangle. The marking of the laser can be achieved, for example, by having one laser of larger power which would translate in the pixel intensity saturation of the projection point.

With respect to the image processing time, it may be preferable to limit the area of the laser projection, for example to a 3 by 3 pixel array. Once, the first laser point has been detected, a search algorithm for the rest of the laser points could be limited to the smaller image matrix, based on the definition of allowable movements.

Other illustrative examples of mathematical calculation that may be used to determine parameters of a pose of the wand and other parameters of pose described herein are included for example in B. K. P. Horn. Robot Vision. McGraw-Hill, New York, 1986; U.S. patent application of Fahraeus filed Mar. 21, 2001 under application. Ser. No. 09/812,902 and published in Pub. No. US2002/0048404 on Pub. Date: Apr. 25, 2002 under title APPARATUS AND METHOD FOR DETERMINING SPATIAL ORIENTATION which discusses among other things determining the spatial relationship between a surface having a predetermined pattern and an apparatus; in U.S. patent of Zhang et al. issued Apr. 4, 2006 under title APPARATUS AND METHOD FOR DETERMINING ORIENTATION PARAMETERS OF AN ELONGATE OBJECT; Marc Erich Latoschik, Elmar Bomberg, Augmenting a Laser Pointer with a Diffraction Grating for Monoscopic 6DOF Detection, Journal of Virtual Reality and Broadcasting, Volume 4 (2006), no. 14, urn:nbn:de:0009-6-12754, ISSN 1860-2037 http://www.jvrb.org/4.2007/1275; Eric Woods (HIT Lab NZ), Paul Mason (Lincoln University, New Zealand), Mark Billinghurst (HIT Lab NZ) MagicMouse: an Inexpensive 6-Degree-of-Freedom Mouse http://citeseer.ist.psu.edu/706368.html; Kynan Eng, A Miniature, One-Handed 3D Motion Controller, Institute of Neuroinformatics, University of Zurich and ETH Zurich, Winterthurerstrasse 190, CH-8057 Zurich, Switzerland http://www.ini.ethz.ch/~kynan/publications/Eng-3DController-ForDistribution-2007.pdf. The content of each of the above references cited above in this paragraph is hereby incorporated by reference into the detailed description hereof.

Rather than using a sensor array to detect the incident spots of light 5 of the beams 4, a camera above a passive surface 1b, as illustrated in FIG. 6a2 may similarly detect the position of the incident spots of light 5 on surface 1 and make the same calculations described above to determine the position and attitude of the wand 2. Alternatively, a camera 3c may be incorporated into the wand 2 to detect where the spots of light fall on the surface 1b, as illustrated on FIG. 6a1.

With reference to FIG. 6, since the space in front of the sensor array(s) may be different from the space that the robot operates in, the operator may reset or, as is usually the case, center the wands 2 in front of the sensor array 1, to coordinate the wand's position with that of the working end of the robotic arms 15b, 15c and 15d, for the next work sequence. Additionally, the travel distances, while relatively the same, between the wands 2 and the working end of the robot arms 15b, 15c, 15d, may differ. For example, where accuracy is critical, the wand 2 may be set to move relatively long distances, to effect a relatively short displacement at the working end of the robotic arms 15b, 15c, 15d. Conversely, where accuracy is not important and quicker movements, over larger distances are desired, the computer can be instructed to translate short length movements of the wand 2 into relatively large distances of travel at the working end of the robotic arms 15b, 15c, 15d. This relationship can be changed by the operator, at any time, by moving a control on the wand 2 or controls 11e on a console 11d. These methods of computer control are well known to the art and embodiments of the invention that incorporate such controls are within the ambit of the invention.

The relative attitude of the sensor array 1 to the attitude of the robot arm work space 14b can also be set, which is usually at the commencement of the work, although it may be changed during the operation. For example, the vertical line in the sensor array 1 will usually be set to be the vertical line in the work space 14b, so that when the wand 2 is raised up vertically in front of the sensor array(s) 1, the robot will produce a vertical motion at the working end 15b, 15c, 15d of the robotic arm. This however may be changed by the operator varying the settings of the vertical and/or horizontal plane at the console 11d or in some other embodiments in the wand 2.

Similarly the longitudinal axis of the wand 2 is generally set as the same as the longitudinal axis of the working end of the robot's arms 15b, 15c, 15d, although this too can be altered by controls at the console and in some other embodiments in the wand itself.

At the start or reset times, the position and attitude of the wand 2 can be translated to be the same as the position of the working end of the robot arms 15b, 15c, 15d; the motions thereafter, until the next reset, can be relative. This allows the operator to change the operator's start or reset position and attitude of the wand to make it more comfortable to execute the next set of procedures, or provide sufficient room for the next set of procedures, in front of the sensor array 1, as referred to above.

The movement of the wands will then control the movement of the tools to which they are assigned by the operator.

Finer movements and movements that require haptic feedback can be effected by controls on the wands 2b, such as the finger hole control 21, the rotary control 20, 20a and the finger slider control 19b, illustrated on FIG. 6c. Switches on the wand or on the console can turn off the active control of the tools by the movement of the wand(s), but may turn on or leave on the active control of the tools by the controls on the wand to prevent inadvertent jiggling or wander while critical and/or fine work is being conducted by the operator. On other occasions the operator may wish to manipulate the wand 2 position simultaneously with moving the controls 20, 20a and 19b or other controls which that preferred embodiment might include.

The sensor array 1 may be made of one or more sheets or panels of light sensor arrays, in which each pixel of the sensor array 1 can communicate the fact that the spot of light 5 has or has not fallen on that pixel to the computer, and identify which light beam 4 and from which wand 2, it originated. When integrated by the computer 11 with other inputs from other locations, this information can identify the location and attitude of the wand 2, by triangulation, mathematic methods and computer algorithms, well known to the art.

In some embodiments the color of the incident light, and/or the addressable pulse frequency of the light that is detected, identifies which particular light beam and wand has cast the light so incident. For example, in some embodiments a wand may have several light-emitting elements, such as a laser, diode laser or light-emitting diode, having a different light wave length (or color), which can be identified and distinguished by the sensor array 1 (in combination with the computer). In other embodiments, the light emitter 3a is modulated or pulsed to give it a unique pulse address, which when its beam 4 is detected by the sensor array 1, which with the computer identifies the particular light beam 4, wand 2 and location and attitude of the same. Other embodiments may take advantage of the relative unique patterns of beams 4 emitted from each wand 2 to identify the wand 2 and perhaps the particular beam 4 from that said wand. Other embodiments can include a combination of these methods, or other similar beam identification methods, well known to the art. It can be desirable to provide additional light emitters 3a to provide redundancy, in the event one or more of the beams does not strike a sensor. For example, in some embodiments an axial reference beam 4 may be directed straight along the longitudinal axis of the wand 2.

One or more of the light beams 4 may be modulated so as to provide information as to the wand 2 identity, and its mode of operation. For example, it might convey information as to the desired heat setting and off/on state of the cauterizing scalpel, or the forceps clasping position, as set by the wand's operator. It might also indicate the rotation of a particular tool. These are only examples of the information that may be selected by the operator, on the wand controls, and then conveyed to the sensor array 1, and hence to the computer to control the robotic arms. Embodiments can include all other convenient instructions and inputs, and all are included within the ambit of the embodiments described herein. This method of conveying instructions may be handled by a dedicated light emitting element 3a, or be bundled into one or more of the light emitting elements 3a that are used to determine the position and attitude of the wand 2. This method of conveying instructions and status information from the wand may be in addition to wireless communications 16, 16a means embedded in the wand, or in place of it.

The pulses of light from the light-emitting elements 3a from cluster 3 of the wands, may be synchronized such that spots of light 5 of the beam 3 fall on the sensor array 1 at discrete times so as to avoid conflicting signals in those architectures that do not have direct connections between the sensor elements and drivers, such as active or passive matrix. In other embodiments, redundant beams are sufficient to resolve any signal interference and software means such as path prediction algorithms can be used to resolve any such conflicts. The beams in most cases will fall on more than one and in most cases many pixels in the sensor array, which will improve reliability, at the expense of resolution, and may also be used to distinguish between two beams that strike approximately the same pixels group.

There are many methods of constructing a light sensor array 1, well known to the art, and includes thin film transistor (TFT) arrays in which there may be included color filter arrays or layers, to determine the color of the incident light and report the location to the computer by direct and discreet connection, or more often, by way of a passive or active connection matrix. These active matrixes or AMT-FT's architectures can be used in some embodiments. Recently, Polymer TFT's sensor arrays are being made which substantially reduce the cost of such sensor arrays. These less expensive arrays will mean that the sensor array(s) 1 can be made much larger. An example of a Polymer TFT, is described by F. Lemmi, M. Mulato, J. Ho, R. Lau, J. P. Lu, and R. A. Street, Two-Dimensional Amorphous Silicon Color Sensor Array, Xerox PARC, United States, Proceedings of the Materials Research Society, 506 Keystone Drive, Warrendale, Pa., 15086-7573, U.S.A. It is understood that any convenient light sensor array may be used, including any future development in light sensor arrays, their architecture and composition, and such an embodiment is within the ambit of the embodiments described herein.

In some embodiments, the sensor array pixels may be combined with light emitting elements, forming a superimposed sensor array and a light emitting array. In these embodiments an image of the working end of the robot arms 15b, 15c, 15d and work sight can be formed on the sensor array 1, and the operator can at the same time view the wand(s) 2 that are initiating the motion of the working end of the robot's arms 15b, 15c, 15d. This embodiment is most effective if the image is generated as a three dimensional image, although this is not required. Methods for creating a three dimensional effect are well known to the art and include synchronous liquid crystal glasses and alternating left eye, right eye, image generation and single pane three dimensional arrays. It is to be understood that the embodiments described herein includes all these methods and future three dimensional image generation methods.

Other embodiments may use an additional camera aimed at the operator's hands and wands, and append the image to that of the worksite that is viewed in the operator viewer 8. This appended image may be turned on and off by the operator.

In those preferred embodiments that use a surface 1b, and camera 3c, in place of the sensor array 1, as illustrated in FIG. 6c, the wand 2b operates partly as a laser or optical mouse, that is, detecting movement by comparing images acquired by the lens of part(s) of the surface 1b. In some preferred embodiments images of spot(s) 5 can be detected by the said lens 3c, noting both their texture or image qualities, and their positions relative to other spot(s) 5. Since the relative angle of the projected beams 4 are known, the computer 11 and/or controller/encoder 18, can process this information to determine the three dimensional position of the wand 2*b* relative to the surface 1*b*, for example by using both methods used by optical/laser mice and mathematical methods including trigonometry, well known to the art. As an example, movement of the wand 2*b* on planes parallel to the surface 1*b*, can be determined by methods used by optical/laser mice, which are well known to the art; and the height and attitude of the wand in three dimensional space can be determined by the lens 3*c* detecting the relative position of the spots 5 projected onto the surface 1*b*, and using triangulation and mathematical methods described above, which are also well known to the art. More particularly, the position of the wand 2*b* in three dimensional space can then be computed by integrating these two information streams to accurately establish both the lateral location of the wand 2*b* and its height and attitude in space. Thus, not all parameters of the pose are determined utilizing the detected pattern of the spots on the surface; rather, some of the parameters are determined utilizing the texture information (lateral location), while other parameters are determined utilizing the detected pattern of spots (height and attitude).

In other embodiments, where there are two or more panels, that are placed at relative angles known to the computer 11, such as those illustrated in FIG. 6*a*1, the wands 2 may contain camera(s) 3*c* which are able detect the position of spots 5 on two or more panels. In these arrangements, where the panels are surfaces 1*b*, the orientation and position of the wand 2 may be determined for example as described above by mathematical methods, including trigonometry. For example, in an embodiment where the panels are arranged at right angles to each other (at 90 degrees), as illustrated in FIG. 6*a*1, and where the angles at which the light beams 4 trace relative to the longitudinal axis of the wand 2 are known, and where the relative positions of the projected spots 5 which fall on both panels are recorded by the camera(s); the position and orientation of the wand 2 in three dimensional space can be directly determined by mathematical methods, including trigonometry.

This information, for example, can then be used to control the tools 15*b*, 15*c*, and 15*d*, or control any process, virtual or real. It can be readily appreciated that the wand 2*b*, like the wand 2 can be any shape and have any function required, for example having the shape of an optical/laser mouse and pointing and directing processes in a similar manner.

In this disclosure, references to wand 2, should be read as including wand 2*b* and vice versa, as the context permits. Similarly references to sensor array 1 should be read as including surface 1 and vice versa, as the context permits.

Embodiments of the invention that incorporate a surface 1*b*, rather than a sensor array(s) 1, pass information from buttons and hand controls, for example 19*a*, 20 and 21, on the wand 2*b* wirelessly or by direct connection, herein described, and by other methods well known to the art. The beams 4 may be encoded for maintaining identification of each beam and each spot 5; for example, the light emitting elements 3*a* may be pulsed at different frequencies and/or have different colors, which the lens 3*c* may detect from the light reflected from the spots 5. Although, a wand 2*b*, may resort exclusively to those methods used by optical/laser mice, to determine its position in three dimensional space, without resort to detecting computing and integrating the relative positions of projected spots 5, the accuracy of such a system will be inferior to those that include those latter methods and the computational overhead will be greater as well. It is to be understood that some embodiments can rely solely on those methods used by optical/laser mice, where accuracy is not as important.

In some embodiments, the surface 1*b* may be any suitable surface including those that contain textures and marks that are typically used in association with optical/laser mice. The surface 1*b* may have reflectivity or surface characterizes, such that the reflected spots 5 that are detected by the camera 3*c* are within a known envelope and thus spots 5 that are off the surface 1*b*, can be rejected in calculating the orientation of the wand 2*b*, accompanied by a warning signal to the operator.

The wands 2, 2*b* may include resting feet that allow them to rest on the surface 1, 1*b*, such that the beams 4 and spots 5 can be detected by the camera 3*c*, and such that the system can calibrate itself with a known wand starting orientation, and if placed on a specific footprint, position; or sensor array 1 or the surface 1*b* may include an elevated cradle 1*e*, as illustrated on FIG. 6*b* to hold the wand 2*b* in a fixed position for the calibration routine. The number of light emitting elements, such as lasers or photo-diodes, will depend upon the accuracy and redundancy required.

The wand 2 may in some applications be stationary, or have an otherwise known position, and measure it's position relative to a moving surface or changing contours on a surface. The embodiments of the invention may include such a wand 2 or be incorporated into a tool, such as those, 15*b*, 15*c*, 15*d*, illustrated in FIG. 15, FIG. 16 and FIG. 17, and be used to compensate for motions, such as the beating of the heart 14*d*1, 14*d*2.

Feedback of forces acting on the working end of the robotic arms 15*b*, 15*c*, 15*d*, may be detected by sensors on the robot arms, by means well known to the art and this real-time information may be conveyed to the computer which can regulate the haptic feedback devices and impart approximately the same forces on the operator's fingers and hands and/or resist the movement of the operator's fingers and hands. These haptic feedback devices, which are well known to the art, can, for example, be incorporated into the controls 19, 19*a*, 20, 21 or 25 other similar controls of the wand 2 or 2*b*. These haptic feedback devices can be active or passive and can impart force on the operator's fingers or hands (active), and/or resist the motion of the operator's fingers or hands (passive). Examples of passive haptic feedback devices are illustrated in FIGS. 19 and 20. FIG. 19 illustrates a passive haptic feedback device in which the flow of an electro-rheological or magneto-rheological fluid is controlled by an electrical or magnetic field. FIG. 20 illustrates a passive haptic feedback device in which the flow of fluid, such as saline or glycerin is controlled by an electro-mechanical valve. Embodiments of this invention may incorporate haptic feedback devices of any design known to the art, and all come within the ambit of the embodiments described herein.

These haptic feedback devices can for example be incorporated into the finger hole 21 sensor/feedback controller 2. For example the finger holes 21 of the wand that is a faux forceps, as illustrated in FIG. 9, can be provided with haptic feedback devices which provide pinching feedback forces to the operator's hands and which accurately simulate the forces acting on the working end of the forceps tool 15*b* on the working end of the robotic arm. The position and motion of the mobile finger hole 21 can be conveyed to the computer wirelessly, by beam modulation, as described above or by cable.

Similarly, the same faux forceps, illustrated in FIG. 9 can on some preferred embodiments of the invention, include a haptic feedback device in the finger slider sensor/haptic feedback device 19*c*, which senses the movement of the finger slider 19*a*, and which can move the forceps tool 15*b*, back and forth in a direction parallel to the longitudinal direction of the said tool 15*b*. As the operator slides the finger slider from 19*a* position to 19*b*, the operator feels the same resistance that the tool 15*b* senses when it pulls back tissue that it grasps, in response to the pulling back of the said slider 19*a*.

The faux forceps, illustrated in FIG. 9 can transform its function from forceps to any other tool or instrument that is required. For example the same faux forceps, illustrated in FIG. 9 can act as a controller for a scalpel tool 15*d*, a wrench 27 (illustrated in FIG. 13), or any other tool or instrument, in which the various controls 19, 19*a*, 20, 21 of the wand are programmed to have different, but usually analogous, functions for each particular tool. The operator can select a particular tool by pressing a particular footswitch, a switch on the wand 2, or other switch location. All tools available and the selected tool may be presented as icons on the operator viewer 8, through the three dimensional eyepieces 9, an example of which is illustrated in FIG. 10 as detailed at 10*h*. For example, the selected tool might be bolded as the forceps icon 26*b* is bolded for the left hand wand 2 in the detail 10*h*, while the wrench tool icon 27*b* is bolded, for the right hand. Once selected, by the operator, the other various controls 19, 19*a*, 20, 21 and other controls, would be assigned to various analogous functions. The operator might call up on the viewer 8 a summary of which controls on the wand relate to what actions of the tools 15*b*, 15*c*, 15*d*, or other applicable tools or actions. All icons may be switched off by the operator to maximize his viewing area through the eyepieces 9.

Some embodiments also include means for reducing latency and accommodating to the motion of the subject.

Further details of the embodiments will now be discussed with particular reference to the FIGS.

FIG. 1 illustrates the operator's hand 6 controlling the motion of the wand 2 within the sensor array 1, comprised of five rectangular segments, forming an open-sided box. FIG. 1 also illustrates the narrow light beams 4 emanating from the light-emitting cluster 3, and projecting spots of light 5 on the light sensors on the inside of the sensor array 1. The light-emitting elements 3*a*, that comprise the light-emitting cluster 3, are usually positioned such that the narrow beams of light 4 that they emit form a unique pattern, so as to aid in identifying the particular wand 2 that is being used. Various embodiments contain various numbers of light-emitting elements, depending upon the accuracy required and whether dedicated information carrying beams are used. Any shape of sensor array 1 can be utilized, and those illustrated in FIG. 1, FIG. 2, FIG. 6*a* and FIG. 6*a*1 are only intended to be examples of a large class of sensor array shapes, sizes and arrangements. The density of pixels or discrete sensors comprising the sensor array 1 will vary depending upon the use to which the robot is put.

FIG. 3 illustrates the three dimensional viewer 8 which includes two eyepieces 9 and feedback information 10 which is superimposed on the image of the work area. As illustrated in FIG. 4 and FIG. 5 the size and orientation of the vectors 10*d* and 10*f*, and the numerical force unit 10*e* and 10*g* can be computer generated to graphically report the changing forces acting on the working end of the robot's tool that corresponds to the wand that is being manipulated. In some embodiments, these vectors are three dimensional views, such that the vector position will correspond with the forces acting on the three dimensional view of the instruments, viewed through the viewer 8. The viewer 8 may superimpose feedback information on additional wands on top of the three dimensional view of the work area. These superimposed views may of course be resized, repositioned, turned on and off by the operator. The view of the work area is captured by a three dimensional camera 15*c*, as illustrated in FIG. 6, which transmits the image information along transmitting means 11*c* to the computer 11 and viewer 8. The position of the camera, like that of any robot tool may be controlled by a separate wand 13, such as that illustrated in FIG. 6, or be controlled by a multi-purpose wand, which changes its function and the tool it controls, by a mode selecting control such as through rotary control 20, which is incorporated into the wand 2, as illustrated in FIG. 7. The camera may also be programmed to keep both tools 15*b* and 15*d* in a single view, or selected tools in a single view. This automatic mode may be turned on or off by the operator, who may then select a wand controlling mode. The feedback reporting means may be presented in many ways and that described is meant to be an example of similar feedback reporting means, all of which come within the ambit of the embodiments described herein.

In some embodiments the viewer 8 is attached to a boom support, so that it may be conveniently placed by the operator. Various preferred embodiments place the controls 11*e* on the console 11*d* which is adjacent to the sensor array 1 and the wands 2, but they may also include foot switches 12, one of which is illustrated in FIG. 6. It can be readily appreciated that the computer 11 may be replaced with two or more computers, dividing functions. For example, the sensor array 1, wands 2, one computer 11 and viewer 8 may communicate at a significant distance with a second computer 11' (not shown) and work site robot controller 15. This connection could be a wideband connection which would allow the operator to conduct a procedure, such as an operation from another city, or country.

The wands 2 and 2*b* illustrated in FIGS. 7, 8, 9 and 12 are only meant to be examples and other embodiments would have different shapes and controls and still be within the ambit of the embodiments described herein. For example, some embodiments may have a revolver shape. FIG. 7 illustrates the principal components of one embodiment. The wand 2 in FIG. 7 contains a rechargeable battery 17 to supply power to the various functions of the wand 2. The terminals 17*a* extend beyond the wand and provide contacts so that the wand may recharge when placed in a docking station which may accommodate the other wands, when not in use. Transmission means 17*b* provides power to controller/encoder 18 from battery 17. Controls 19, 20 and 20*a* are meant to be illustrative of control means, to switch modes of operation, such as from a cauterizing scalpel to a camera or forceps; and/or to vary the heat of the cauterizer or the force applied to the forceps grippers, to name just a few examples. In those cases where the robot arms are snake-like, these controls 19, 20 and 20*a* or similar controls, may control the radius of turn, and location of turns, of one or more of the robot's arms. In FIG. 7 transmission means 19*a* connects a lever control 19 to the controller/encoder 18; transmission means 20*b* connect the rotary controls 20 and 20*a* to the controller/encoder 18.

The controller/encoder 18 in some embodiments pulse the one or more of the light emitters 3*a* to pass-on control information to the computer, via the sensor array 1, as mentioned above. Transmission means 3*b* connects the emitters to the controller/encoder 18. The light-emitting array 3 may contain discrete emitters; they may also be lenses or optical fibers that merely channel the light from another common source, for example, a single light-emitting diode or laser. Other wireless means may be included in the wand 2, which require an aerial 16a which communicates with an aerial 16 in communication with the computer 11, as illustrated in FIG. 6.

While the wands illustrated are wireless, it should be understood that various other embodiments may have wired connections to the computer 11 and/or to a power source, depending upon their use, and these embodiments come within the ambit of the invention. In some embodiments, such as those in which the wand 2 is connected directly to the computer 11, the controller/encoder 18 and all or parts of its function are incorporated into the computer 11.

FIG. 8 illustrates a faux set of forceps 2b, which give the operator or surgeon the feel of the forceps he may use later in the same procedure or another day when the robot is not available or suitable for the operation. FIG. 8 is meant to be illustrative of designing the wand to resemble instruments or tools that would be otherwise used in a manual procedure. This allows the skills learned using these devices to be used when controlling a robot and reduces dramatically the learning time required to use the robot effectively. While embodiments may include wands of many shapes, and configurations, those that resemble in function or appearance the tools or instruments that are normally used, are particularly useful to those situations where the operator must carry out similar procedures both manually and by robot.

FIG. 8 illustrates a faux forceps wand 2b which has two finger holes 21, one of which pivots at the controller/feedback device 21b, which detects motion of the movable finger hole 21, which is transmitted by transmission means 21d to the controller/encoder 18 which then transmits the motion wirelessly, or directly, to the computer 11 or encodes pulses by modulating the output of the light emitters 3a, the light beam produced transmitting the motion and position of the movable finger hole 21 to the sensor array, and subsequently the computer 11. FIG. 8 also illustrates an alternative method of detecting and transmitting changes in the position of the various control elements on the wand 2b. Emitter(s) 3a may be placed on the movable elements, such as the finger hole 21. The projected light 4 that is incident on the sensor array 1 or surface 1 may then be used by the computer 11 to determine the position of the moving element, as it moves, such as the finger hole 21, illustrated in FIG. 8. This method of detecting and reporting the movement of control elements may be used in any such elements which are contained in various embodiments of the invention. For diagrammatical simplicity the connection from the light emitter 3a, on the finger hole 21, to the controller/encoder 18 has not been shown.

The controller/feedback device 21b may also receive instructions wirelessly or by direct connection from computer 11, which directs the magnitude and direction of haptic feedback forces on the pivoting action of the movable finger hole 21. These haptic feedback forces can be passive or active, depending upon the design of the controller/feedback device. In some embodiments, no haptic feedback component is incorporated into the controller/feedback device, and in these embodiments the controller/feedback device 21b merely transmits motion and position data of the movable finger hole 21 to the computer, via the sensor array, wirelessly or directly to the computer 11.

FIG. 8 also illustrates a notional end 4a for the wand 2b which the operator sets at the console 11d to allow for sufficient room between the ends of the wands 2b, when the tools are in close proximity.

FIG. 8a, and detail drawings 8b and 8c, illustrate a wand 2 similar to FIG. 7, but instead of multiple fixed emitters 3a, there is one or more emitters 3a, the beam(s) 4 of which are redirected by a mirror(s) 3d or other beam redirecting device. In this embodiment, the controller/encoder 8 directs each mirror 3d in the mirror array 3e, housed in a transparent housing 3f, and secured to it by rod supports 3g, to redirect part or the entire beam 4 produced by the emitter 3a. As illustrated in FIG. 8b, the controller/encoder 18 and/or the computer 11 selects each mirror 3d1 and varies its angle relative to the mirror array 3e (one at a time or in groups) and, with other mirrors in the array, directs the beam(s) in a programmed sequence, noting the angle of the projected beam relative to the wand 2 and simultaneously comparing this to the point(s) 5 detected on the surface 1b, and by mathematical means, including trigonometric methods, defining at every selected pair, at that point in time, the position of the sensor relative to the surface 1b (or sensor array 1 in those embodiments where a sensor array is used to detect the spot 5). Embodiments include all means of redirecting the beam 4, including solid state electronic mirror arrays, such as those developed by Texas Instruments Corp. or mechanical or other optical redirecting devices well known to the art. The solid state mirror arrays that have been developed by Texas Instruments Corp. may incorporate any number of mirrors and may incorporate thousands of them, each of them or groups of them being controlled by electronic means. This system is one of a larger class known as microelectronic mechanical systems (MEMS). Because the beam can be programmed to quickly produce multiple pair inputs at various angles, for mathematical comparison, as described above, the controller/encoder 18 and/or computer 11 can calculate the position of the wand 2 in three dimensional space at each point in time. The beam may be directed in various patterns, and may adapt the pattern so as to maximize the coverage on the sensor array 1 or surface 1b and minimize or eliminate the occasions in which the beam would fall incident outside of the perimeter of either the sensor array 1 or the surface 1b.

Other embodiments, such as that illustrated in FIG. 8a, may include a motor or motive device rotating mirror or prism, in place of the mirror array 3e, which redirects the beam 4 and, for example, may project an ellipse (when stationary, and open curves, when the wand 2 is in motion) or other set of curves, on the sensor array 1 or surface 1b. In such a case at every point in time the controller/encoder 18 and/or computer 11 can calculate the position of the wand 2, as at each point in time the angle of the beam emitted, relative to the wand, is known and matched with its other pair 5 that is projected on the sensor array 1 or surface 1b at that same point in time. Obviously, the rate of rotation must be sufficient so that every motion of the wand 2 is captured by the sensor array 1, or camera 3c. Since the controller/encoder 18 and/or the computer 11 direct the mirrors in the mirror array and control the angle at every point in time each mirror elevates from the mirror array 3e surface, the angle at which the beam 4 is redirected, relative to the wand 2 is known, speeding the mathematic calculation, described above. As illustrated in FIG. 8c, any number of beams may be actuated at the same time, some being pulsed, panned about, while others may stay on, and may be fixed or be set at various angles. For example, FIG. 8c illustrates how mirrors 3d2 and 3d3 may be elevated at different angles, producing divergent beams 4, with a known angle. Also, by way of further example, an embodiment in which the wands 2 incorporate a camera(s), which may be located on various parts of the wand or some other convenient location, some beams may stay on so that the camera 3c can record the surface patterns, which assist in locating the position of the wand 2, in three dimensional space, relative to the surface 1b.

In other embodiments, as illustrated in FIG. 8d, shapes such as, circles or ellipses are projected on the sensor array 1 or surface 1b by optical means, such that the changing shapes, define the orientation and position of the wand 2b. For example, a single light emitter 3a, may include a lens, or other optical device, which converts the light beam into a cone, which may project a ring of light; or a field of light having the same outside boundary as the ring type (herein called a filled ring) onto the sensor array 1 or surface 1b. In most embodiments a ring (not filled) is preferred, as the amount of data that requires processing is reduced, however a filled ring or field may be used for some embodiments. The three dimensional orientation and position of the wand 2, 2b may be calculated by comparing the projected shape and the detected shape that is detected on the sensor array 1 or surface 1b, by various mathematical means well known to the art such as projection geometry and trigonometry. For example, a light emitter 3a and dispersing lens which projects a circle onto the sensor array 1 or surface 1b, when the longitudinal axis of the wand 2 is normal to the said sensor array 1 or surface 1b, may for example project a parabola, when tilted off the normal. The computer can use this change in shape to calculate the orientation and position of the wand 2 with respect to the said sensor array 1 or surface 1b. It can be readily appreciated that the shapes 5c, illustrated in FIG. 8d, are in fact equivalent to a string of points 5 illustrated in FIG. 1 and FIG. 6a. The advantage is that a single emitter 3a including a dispersing lens(s) may be used rather than a series of emitters 3a. The other advantage is there is greater redundancy. On the other hand, a few discrete points of light 5 require far less computation than many points, and where speed of movement is important, a few points of light are preferable. The embodiment illustrated in FIG. 8d may be used with a sensor array 1b in which the projected shape 5c, comprised of spots of light 5, is sensed and reported to the computer 11, or one in which a camera 3c on the wand 2, or remote from it, is used to record the projected shapes 5c. As illustrated in FIG. 8d, where a camera 3c is used for detection, in addition to those means described above for determining the position of the wand 2b, a coded grid 1c, may be applied to the surface of surface 1b. The grid may be coded, in a similar way to a bar code, such that the position of the shape 5c or points 5 can be viewed by the camera 3c and their absolute position on the surface can be reported by the camera to the computer 11, to calculate the orientation and the position of the wand 2b in three dimensional space. As illustrated in FIG. 8d, the bar code grid may be formed from two bar coded patterns, superimposed at right angles. Any spot on the surface 1a, will then have a unique address, defined by the adjacent group of bars. The thickness, of the bars and their relative separation from each other may be arranged to encode locational information, by means well known in the art. Since the computer 11 has the same grid in memory, it can make a simple pattern match, or other method, well known in the art, to determine the location of each point of light that forms the shape 5c or for that matter any spot 5 which other embodiments of the invention rely on, such as those illustrated in FIG. 6a and FIG. 6a1. At any point on the surface, there will be a unique address defined by the two patterns immediately adjacent to the spots 5 and shapes 5c. These patterns will form the nearest address to each point at which the spots 5 and shapes 5c are incident. Since the computer has stored in memory the grid, it can then refine the position of each of the incident spots 5 and shape 5c, by noting the displacement of the said spots and shapes from the nearest bars, the exact position of which is in the computer memory. Some spots 5 and shapes 5c may by happenstance fall on the intersection of two bars, in which event the displacement calculation may not be necessary. It should be appreciated that while reference has been made to a bar code type of indexing system, other encoding schemes may be used in other embodiments and be within the ambit of the embodiments described herein.

FIG. 9 illustrates a wand 2b that includes a sliding finger control 19a with associated controller/feedback device 19c which functions in a similar manner to the movable finger hole 21, except that the sliding finger control 19 provides a convenient means of conveying linear motion to the robot tools. In the example illustrated in FIGS. 9 and 11, when the sliding finger control 19a is moved to position 19b, a distance of 19d, the controller/feedback device instructs the computer 11 to cause the tool, in this example 26, to move a given distance 19d in a similar linear direction, as assumed by 26a in FIG. 11. As mentioned above, the operator may set the ratio between the motion of the sliding finger control 19a and the consequent motion of the tool 19a, thus these distances may be different, even though relative. Simultaneously, the operator may squeeze the finger hole control 21, to position 21c, a displacement of 21d, to instruct the fingers of tool 26 to close a distance of 21d to assume the configuration of 26a in FIG. 11. As referred to above, haptic feedback may be provided by the controller/feedback controller 21b by means described above.

FIG. 10 illustrates the operator viewer 8, while the tool 26 is being manipulated, as illustrated in FIGS. 9 and 11. In this example the operator is manipulating wand 2/2b in his left hand. The left tool icon display 10h has bolded tool icon 26b, which indicates that the operator has chosen tool 26 to be controlled by his wand, such as that illustrated in FIG. 9. The right tool icon display 10h has bolded tool icon 27b, which indicates that the operator has chosen tool 27, as illustrated in FIGS. 12, 13 and 14, to be controlled by his wand 2, such as that illustrated in FIG. 9.

FIGS. 12, 13, and 14, illustrates that rotary motion at the tools can be controlled from a wand, such as that illustrated in FIGS. 9 and 12. In this example of the invention, the movable finger hole control 21 can be squeezed by the operator, displacing it a distance of 21d to position 21c, which causes the tool 27 to close a distance of 21d, gripping bolt head 29, assuming configuration 27a, as illustrated in FIG. 13. Simultaneously, the operator moves the finger slider control 19b a distance of 19d, to assume position 19a, to move the tool forward a distance of 19d, toward the bolt head 29, as illustrated in FIG. 13. The operator may then choose to rotate the bolt head by rotating roller control 20 a distance and direction 20b, to move the tool in direction and distance 20b, to assume-position 27c. The controller/feedback controller 20c senses the motion and position of the roller control 20, and may impart haptic feedback, in a similar manner as described above in relation to the finger hole control 21, above.

While the disclosure and examples of the invention above are in the context of a guiding device that is controlled by the operator's hands, and describes the attitude and position of the wand 2, 2b in three dimensional space, it should be understood that the guiding device may be used to describe the relative motion of a surface, where the wand or guiding device is fixed, or its position is otherwise known. For example FIG. 15 and FIG. 16 illustrate the movement of the surface 14d1, 14d2 of the heart as it beats. In this case the components of the wand 2, 2*b* are incorporated into the distal end of the camera tool 15*c*, although they may be incorporated into any other tool as well, and come within the ambit of the invention. The emitter cluster 3 and emitters 3*a* may be seen in greater detail in FIG. 18. It should be noted that this example of the emitter cluster 3 which uses any number of emitters 3*a*, can be replaced with any of the other types of emitter clusters, including mirror arrays or articulating mirrors and prisms, referred to above. The angles between the beams 4, including Θ1, Θ2, and Θ3, and the angles between the beams 4 and the tool 15*c* as illustrated in FIG. 18 are known to the computer 11, in calculating the surface topology 14*d*1 and 14*d*2 as illustrated in FIG. 18. As illustrated in FIG. 17, the stereo camera 3*c*1 and/or 3*c*2 record the spots 5*a* and 5*b* projected on the surface of the heart 14*d*1, 14*d*2. It can be readily be appreciated that as the heart beats, the surface 14*d*1 and 14*d*2 moves up and down, and the spots projected on the surfaces, including 5*a* and 5*b*, change their distance from their neighbors 5*a* and 5*b* on their respective surfaces. This distance change, along with the angle of the beam, is recorded by the camera or cameras, 3*c*1 and/or 3*c*2, and this information is processed by the computer 11, which computes the distance of those parts of the surface from the distal end of the camera tool 15*c*, using trigonometric and other mathematical methods, well known to the art. It should be noted that this information also provides the distance between the surface and any other tool, such as 15*b* and 15*d*, as illustrated in FIG. 15 and FIG. 16, as the relative position of the tools is known, but positional sensors incorporated into the said tools. The more spots 5 (in this illustration referred to as 5*a* and 5*b* to denote their change in position) that are projected at any given time, the greater will be definition of the changing topology of the surface and its distance from the distal end of the tools, 15*a*, 15*b* and 15*c*, and any other tools that may be used. Various shapes or patterns, such as grid patterns may be projected onto the surface of the heart, by various optical means, herein described, or well known to the art. These shapes or patterns may be considered as strings of spots 5, 5*a* and 5*b*.

As the heart beats, and the distance between the distal ends of the tools and the heart surface 14*d*1 and 14*d*2 varies, the computer can instruct the tool arms to vary their length to keep the distance between the surface and the distal end of the tools constant (assuming the operator has not instructed any change in tool position). In the example illustrated in FIG. 15 and FIG. 16, the arms are telescoping, for example, the arm 15*c*, the camera arm, has a distal shaft which can slide in and out of the main arm 15*d*. In FIG. 15 the distal shaft 15*c*1 is relatively extended, so that it is located in an ideal position to view the distal end of the other tool shafts, 15*b*1 and 15*d*1 which are positioned, in this example, immediately above the surface 14*d*1 of the heart. As the surface of the heart moves up, as illustrated in FIG. 16 and FIG. 17, the movement is detected by the changing lateral separation between the neighboring dots, such as dots 5*a* and 5*b*, and their respective neighboring dots on their respective surfaces. The computer may use this information, using trigonometric calculations and other mathematical techniques, well known to the art, to direct the arms to move up sufficiently, so as to keep the distal end of the tools, 15*b*2, 15*c*2 and 15*d*2 at the same relative distance to the heart surface 14*d*2. As can be appreciated, this dynamic adjustment of the tool arm length can effectively compensate for the motion of the beating heart, allowing the operator to control other tool motions (which overlay the compensating motions) and which actually do the work, just as if the heart were stationary. As mentioned above, lateral movements of the heart surface 14*d*1 and 14*d*2 can also be compensated for by using texture and pattern recognition methods utilizing the surface that is illuminated by the spots 5*a*, 5*b* and 5 (in addition to areas, not so illuminated). For this purpose, the spots 5 may be considerably larger to incorporate more textural or pattern information. The vertical and lateral means of characterizing the motions of the heart surface can then be integrated by the computer 11 and any motion of the heart surface can be fully compensated for, effectively freezing the heart motion, to allow for precise manipulation of the tools, for example, to cut and suture the heart tissue. The integration of this information will provide information on the bending, expansion and contraction of the surface, in addition to (in this example) the changes in elevation of the surface. Fortunately, as the surface that is being worked on by the surgeon is small, this additional characterization (ie. bending, expansion and contraction) is most often not required. It should be noted that as the camera tool 15*c* is making compensating motions, the operator's view of the heart surface will remain the same, ie the heart will appear to virtually stop, and any more complex movements, ie. stretching and shrinking and localized motions may be compensated by software manipulating the image, by means well known to the art. Similarly, rather than the camera tool 15*c*, making compensation motions, the image presented to the operator can by optical and electronic means be manipulated to give the same effect. For example in some embodiments of the invention, the camera lens may be zoomed back as the surface of the heart advances toward it, giving the effect of an approximately stationary surface. The operator may of course choose to override any or some compensating features of the system. The operator may also choose to select the area of the surface of the heart or other body, for which motion compensation is required. This may involve selecting a tool, such as the sensor cluster 3, with varying angles of emitter 3*a* angles, or instructing the computer to compute only those changes within a designated patch, which might be projected on the operator viewer 8. In most cases the area of relevant motion will be small, as the actual surgical work space is usually small. The operator may, or the system may periodically scan the surface to define its curvature, especially at the beginning of a procedure.

The stereo camera's 3*c*1 and 3*c*2 may also provide distance information, using parallax information and trigonometric and standard mathematical methods well known in the art of distance finders. Other optical methods of distance determination, such as is used in auto-focusing cameras and medical imaging, and well known to the art, may be used as well, and be within the ambit of the invention, such as Doppler detection and interferometry. This information, acquired by all these methods, may be used to supplement or backstop the other distance information, which is acquired by methods described above and integrated by the computer 11. It should be noted that embodiments that use one or more of these methods is within the ambit of the embodiments described herein.

In some embodiments, the computer 11 may receive information from the electrocardiogram (ECG) 14*c*, which has sensors 14*e* on the patient's abdomen and which indicates that an electrical pulse has been detected, which will result in a muscular response of the heart tissue, and hence a change in the shape and the position of the heart surface. The time delay between receiving the electrical triggering pulse and the actual resulting heart muscular activity, even though small, allows for the system to anticipate the motion and better provide compensating motions of the length and attitude of the robot's tools, 15*b*, 15*c*, and 15*d*. The system software can compare the electrical impulses, as detected by the ECG, with the resultant changes in the shape and position of the heart wall, as observed by the methods described above, to model the optimum tool motion that is required to virtually freeze the heart motion. In combination with the methods of motion compensation described above, the inclusion of the ECG initiating information, generally allows for a smoother response of the tools to the motion of the surface it is accommodating to.

It can be readily appreciated that the system herein described allows many surgical procedures to be conducted without resort to a heart lung machine or to other heart restraining devices, all of which can have serious side effects.

It should be readily appreciated that embodiments that compensate for the motion of bodies being manipulated, whether fine grain or course grain, (as chosen by the operator) inherently reduce the effects of latency between the operator's instructions and the motion of the tools, which he guides. This effective reduction or elimination of latency means that telesurgery over great distances, which increases with distance, becomes more practical. The system's software distinguishes between operator generated motion, such as the lifting of a tissue flap, and non-operational motion, such as the beating of the heart. Generally, the former is much finer grained and the latter larger grained. For example, the software may set the compensating routines to ignore small area of motion, where the procedure is being executed, such as the suturing of a flap, but compensate for grosser motions, such as the beating of the heart, which causes a large surface of the heart to move. The design of this software and the relative sizes of the body to which the compensation routine responds or ignores, and their location, will depend upon the particular procedure for which the system is being utilized.

FIG. 21 illustrates an embodiment, which includes additional means to overcome temporal latency between the operator's instructions and the actual tool movements, any of which may be used separately or in combination with the others. FIG. 21 illustrates the operator's view of the worksite as viewed through the viewer 8 and eyepieces 9 illustrating the superimposed tool cursors 15*d*3 and 15*b*3 which illustrate the operator's intended position of the tools at the worksite. These cursors are no normal cursors, they show the exact intended position of the working edges of the tools they control. FIG. 21 also illustrates that the operator also sees the latest reported actual position of the tools 15*d*2 and 15*b*2 at the worksite, the difference between the two being due to temporal latency. The superimposed tool cursors 15*d*3 and 15*b*3 can be electronically superimposed onto the operator's view, and these show the intended position, while 15*d*2 and 15*b*2 show their most recently reported actual position. In most preferred embodiments the cursors are rendered in 3-D, and change perspective, to conform to the 3-D view of the worksite, are simple outlines, so as not to be confused with the images of the actual tools, and may be manually tuned on and off, or automatically presented when the system detects that latency has exceeded a preset threshold. The intended tool position cursors, 15*d*3 and 15*b*3 may also change color or markings to indicate the depth to which they have passed into the tissue, as indicated 15*d*4 in FIG. 21. The cursors 15*d*3 and 15*b*3 may also change color markings in response to forces acting on the actual tools 15*d*2 and 15*b*2, so as to prevent the operator from exceeding a safe threshold for that particular substrate he is manipulating.

FIGS. 29*a* to 29*e* illustrate an example method of limiting the effects of latency in transmission of tool instructions and movement of the body relative to the position of the tools at the remote worksite. Each video image at the worksite FIG. 29*b* is recorded, time coded, and transmitted to the operating theatre, along with the time code for each video frame. The operator at the operating theatre, then sees the video frame FIG. 29*a*, and then causes the tool 15*d*2 to advance along the incision 14*a*, which he views as an icon 15*d*3 in FIG. 29*c*, and the displacement between 15*d*3 and 15*d*2 being the measure of latency. The position of the cursors, that is, the intended tool positions, are transmitted to the remote worksite along with the corresponding frame time-code, of the operator's video frame at each time step. In most embodiments of the invention, the time-code is originally encoded onto the video stream at the remote work site by the remote worksite robot controller 15 which also saves in memory the corresponding video frame(s). As a separate process, and at each time step, at the remote work site, the position of the tools are adjusted to accommodate to their intended position relative to the changing position of the body, as described above, which is illustrated as the accommodation of tool position 45 in FIG. 29*d* and becomes the real time image for the comparison to follow. Upon receiving each instruction from the operator, the worksite controller 15 then retrieves from memory the corresponding video frame and notes the intended machine instruction relative to it. It then compares this frame FIG. 29*b*, retrieved from memory with the real time image at the remote worksite FIG. 29*d*, and carries out the intended machine instruction embedded in FIG. 29*c* resulting in the performance of the intended instruction as illustrated in FIG. 29*e*. This comparison may be accomplished by pattern recognition methods well known to the art which note the relative location of such features as protruding veins and arteries and other visible features. In some embodiments, markers suitable for optical marker recognition 40 are placed on or detachably attached to the operation surface, such as the heart 14*d* to assist in tracking movements of the worksite. While the normalization process, including pattern recognition and other means noted above impose a system overhead on computations, the area that is monitored and the precision of monitoring can be adjusted by the operator. The area immediately adjacent to the present tool position can have, for example, fine grained monitoring and normalization, whereas more peripheral areas can have, for example, coarser gained treatment.

As illustrated on FIG. 21 and FIG. 29*c*, the operator's intended movement of the tools as illustrated to him by cursors 15*b*3 and 15*d*3, may diverge from the actual tools that he views 15*b*2, 15*d*2 the difference being the latency between the two. The operator will immediately know the degree to which latency is occurring, and he may choose to slow his movements to allow the actual tools, 15*b*2 and 15*d*2 to catch up. In some embodiments the systems stops in the event a preset latency threshold is exceeded. It is important to note that the operator, when he stops the tool, will know where it will stop at the worksite. For example, in FIG. 21 the operator is making an incision which must stop before it transects artery 38. Even though the tool 15*d*2 will continue to move forward, they will stop when the meet the intended tool position indicated by cursor 15*d*3, just short of the artery 38. While this disclosure has described cursors resembling a scalpel and forceps and their corresponding cursors, it should be understood that these are merely examples of a large class of embodiments, which include all manner of tools and instruments and there corresponding cursors, and all are within the ambit of this invention.

FIG. 19 and FIG. 20 illustrate two exemplar passive haptic feedback modules that can be incorporated into the controller/feedback controllers in the wand 2, such as 19*c*, 20*c* and 21 *b*. Other haptic feedback devices, well known to the art, whether active or passive, may be incorporated into the controller/feedback controller, and all such systems are within the ambit of the invention.

FIG. 19 is a typical passive haptic feedback device 30 in which the flow of an electro-rheological or magneto-rheological fluid is controlled by an electrical or magnetic field between elements 36, which can be electrodes or magnetic coils. The control of the flow of this fluid affects the speed with which piston 31*a* can move back and forth through the cylinder 31. The piston is connected and transmits motion and forces to and between the piston and the various control input devices on the wand 2, for example, the movable finger hole 21, the finger slider control 19*b* and the roller control 20. The total displacement of the piston 19*d* may for example be the same as the displacement 19*d* of the finger slider control 19*b*, or may vary depending upon the mechanical linkage connecting the two. The working fluid moves 35 between each side of the piston 31*a* through a bypass conduit 32, where its flow may be restricted or alleviated by varying the electrical or magnetic field imposed on an electro-rheological or magneto-rheological fluid. The controller/encoder modulates the electrical energy transmitted by transmitting means 34*a* to the electrodes or coils 36. In other passive haptic feedback devices a simple electromechanical valve 37 controls the flow 35 of working fluid, which may for example be saline or glycerin, as illustrated in FIG. 20. The controller/encoder modulates the electrical energy transmitted to the electromechanical valve 37 which is transmitted by transmitting means 37*a*, as illustrated in FIG. 20.

In both the haptic feedback devices 30 illustrated in FIGS. 19 and 20, a motion and position sensor 33, transmits information on the motion and position of the piston 31*a* by transmission means 34 to the controller/encoder 18. The controller/encoder 18 receives instructions wirelessly 16*a*, or directly from the computer, and sends motion and position information received from the motion and position sensor 33 to the computer.

FIG. 22 is wand 2*b* which may be attached to any body part, tool, or other object, by means of connectors 42 and 42*a*, which have complementary indexing means 42*c* and 42*b*, to ensure their proper alignment. By such means, and similar connecting means, well known to the art, these wands 2*b* may be placed on a body part, such as the surface of the heart 14*d*1 to project the beams 4 to a sensor array 1 or surface 1*b* (not shown) and thereby establish the orientation and position of the heart as it moves. Similarly a wand 2*b* may be connected to any object to determine its position and orientation in space, together with the means hereinbefore described, in cooperation with computer 11.

FIG. 23 illustrates how multiple wands 2*i*, 2*ii* may be used in combination to provide accurate alignment between two or more objects in space. In this example FIG. 23, one wand 2*i* is connected to a drill 44. The other wand 2*ii* is connected to a bone nail 45 with a slotted proximal end, for indexing position, and which has a hidden hole 46 which will receive a bolt, once a hole is drilled through bone 46, and the hidden hole 46 in direction 41. Since the position and orientation of the hidden hole 46 relative to the end of the bone nail, connected to the wand 20*d* is known, the operator can drill a hole along an appropriate path, which is provided by computer 11 calculating the appropriate path and graphically illustrating the proper path with a graphical overlay of the bone shown on viewer 8. The position of the wands 2*i* and 2*ii* in space is determined by those means hereinbefore described. While FIG. 23 illustrates a single sensor array 1, it should be understood that any number is sensor arrays or surfaces 1*b*, might be used, so long as their position and orientation are known to the computer 11, and in the case of surface 1*b*, the camera 3*c*, which would be incorporated into the assembly, as illustrated in FIG. 22, can identify each screen by means of identifying barcodes or other identifying marks. In FIG. 23, the sensor array 1 is above the operating space. FIG. 23 also illustrates two connectors 42*a* that are fixed to a calibrating table 43, which is calibrated in position to sensor array 1. This permits the wands 2*i* and 2*ii* to be connected to the said connectors 42*a* on calibrating table 43 to ensure accurate readings when ambient temperature changes might affect the relative angles of the beams 4, or the distance between emitters 3*a*. The computer 11 can recalibrate the position of the wands 2*i* and 2*ii* by noting the pattern of spots 5 that are projected onto the sensor array 1. While the example shown in FIG. 23 illustrates two wands 2*i* and 2*ii*, any number of wands may be used for purposes of comparing the position of objects, to which they are connected, or changes in position of those objects over time. For example, a one wand might be connected to the end of a leg bone, while another might be attached to prosthesis, and the two might be brought together in perfect alignment. Another example would be connecting a wand 2*i* to a probe of known length, and another wand 2*ii* to a patient's scull, in a predetermined orientation. The wand 2*i* could then be inserted into the brain of a patient and the exact endpoint of the probe could be determined. The wand 2*i* could also be attached to the tools 15*b*1, 15*c*1 and 15*d*1, as illustrated on FIG. 15 to ensure perfect positioning of the tools. For example one tool might have a drill attached, such that the drill illustrated in FIG. 23, is controlled robotically and in coordination with the position of the bone nail 45 in that of FIG. 23. Due to modern manufacturing processes, the wand 2*b* illustrated in FIG. 22, the wand 2*i* illustrated in FIG. 23, and sensor array assemblies 1*d* illustrated in FIG. 24, can be made to be very small and placed as an array on objects such as cars, bridges or buildings to measure their stability over time. Others might be connected to the earth to measure seismic or local movements of the soil. These wands 2*b*, 2*i*, might also be connected to scanners to allow for the scanning of three dimensional objects, since these wands can provide the information as to the scanner's position in space; the scanning data can be assembled into a virtual three dimensional output. Since the wands 2*b* and 2*i* may be put on any object, the uses for assembling objects are countless.

While FIG. 23 illustrates a system in which the camera 3*c* is located in the wand 2, it should be understood that a surface 1*b*, as illustrated in FIG. 6*a*1, or a separate camera 3*c* could be used, as illustrated in FIG. 6*a*2, all of which can detect the position of the incident spots 5.

FIG. 24 illustrates a similar arrangement of wands 2*i* and 2*ii* as illustrated in FIG. 23, but the wand 2*ii* is replaced with sensor array assembly 1*d*. The sensor array assembly 1*d* uses a sensor array 1, which senses the position 5 of the incident beams 4 and reports their coordinates by connection 11*a* to controller/encoder 18 and then wirelessly to the computer 11 (not shown). This system provides the same positional information as that system illustrated on FIG. 23, except that the large sensor in FIG. 23 has been replaced with a much smaller sensor in FIG. 24, making it more economical for certain purposes.

Figure 25:
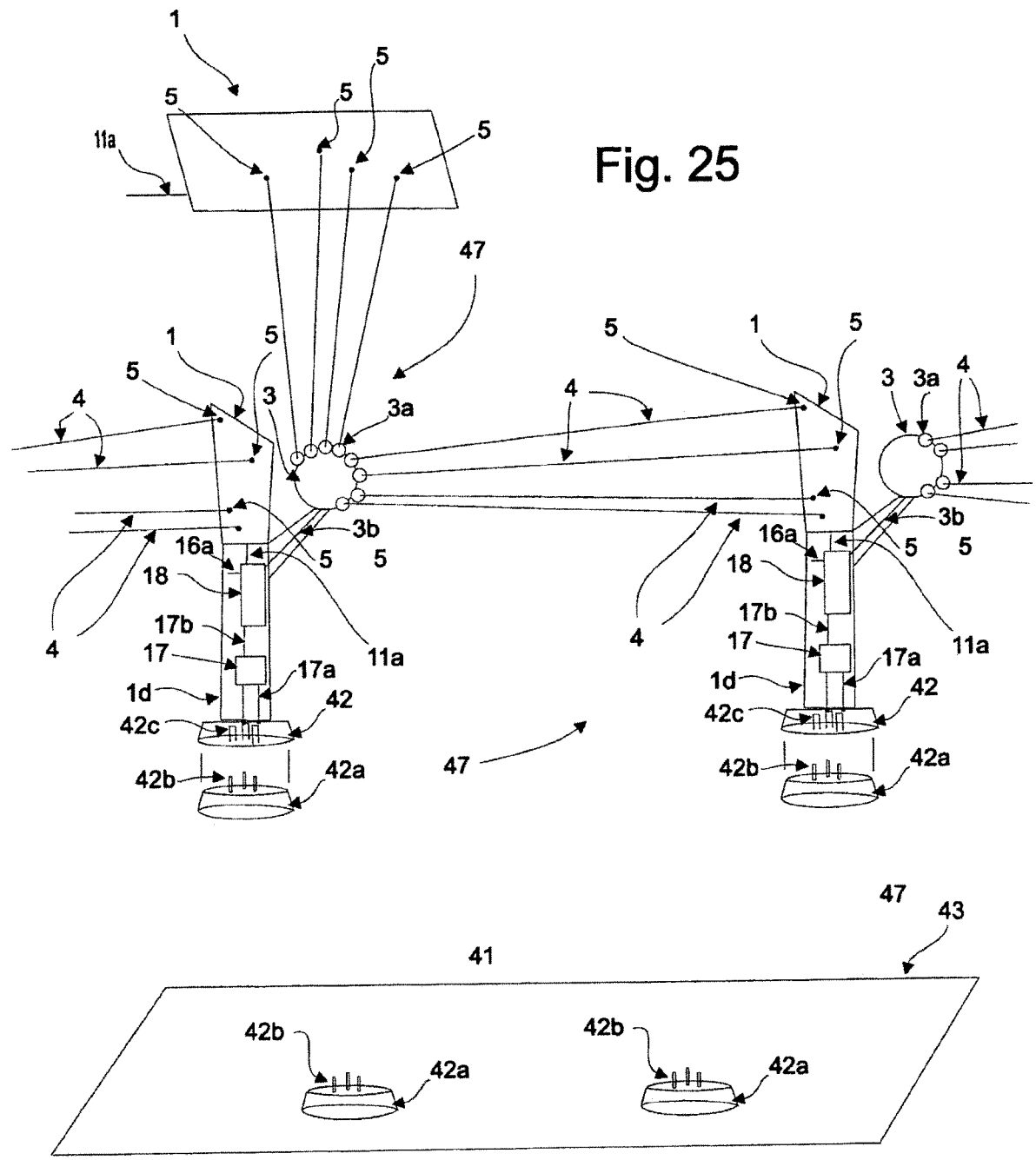
FIG. 25 is a cross-sectional, perspective view of two combination wand and sensor array assemblies 47 which have been daisy chained with two other combination units (not shown and in combination with a sensor array 1.

Referring to FIG. 25, a cross-sectional, perspective view illustrates two combination wand and sensor array assemblies 47 which have been daisy chained with two other combination units (not shown). Such arrays may also be combined with sensor arrays 1 or surfaces 1*b* for greater accuracy. Such arrays can be used to detect and report the relative movement of parts of structures, to which they are attached, such as bridges, ships and oil pipelines.

While embodiments have been described with respect to a system comprised of three tools 15*b*, 15*c*, and 15*d*, it is to be understood that any number of tools and any number of wands 2 may be used in such a system.

While embodiments have used examples of tools that a robot could manipulate, it is to be understood that any tool, object or body may be moved or directed by the methods and devices described by way of example herein, and all such embodiments are within the ambit of the embodiments herein.

While embodiments have been described as being used as a surgical robot, it is to be understood that this use is merely used as a convenient example of many uses to which the robot could be employed, all of which come within the ambit of the embodiments described herein.

While embodiments have been described as being used to manipulate tools, it is to be understood that the methods and devices described by example herein may be used to manipulate virtual, computer generated objects. For example, embodiments may be used for assembling and/or modeling physical processes, such as molecular modeling and fluid dynamics modeling to name just a few.

It is to be understood that modifications and variations to the embodiments described herein may be resorted to without departing from the spirit and scope of the invention as those skilled in the art will readily understand. Such modifications and variations are considered to be within the purview and scope of the inventions and appended claims.

What is claimed is:

1. A robotic surgery system comprising:
a display configured to display information to a user; and
a processor configured to:
receive an image of at least a portion of a surgical site;
cause the image to be displayed on the display; and
in response to a determination that a first instrument has been made available for use at the surgical site, cause a first icon representing the first instrument to be displayed on the display, the first icon indicating to the user that the first instrument is available for use at the surgical site.

2. The system of claim 1, wherein the processor is further configured to:
cause the first icon representing the first instrument to be displayed in a first region of the display; and
in response to a determination that a second instrument has been selected and made available for use at the surgical site, cause a second icon representing the second instrument and indicating to the user that the second instrument is available for use at the surgical site to be displayed in a second region of the display, the second region being different from the first region.

3. The system of claim 2, wherein the first region and the second region are positioned within a region occupied by the image on the display.

4. The system of claim 2, wherein the processor is further configured to cause resizing, repositioning, or turning off the second icon.

5. The system of claim 1, wherein the processor is configured to cause the first icon representing the first instrument to be displayed on the display by causing a portion of the first icon to be bolded.

6. The system of claim 1, wherein the processor is further configured to cause resizing, repositioning, or turning off the first icon.

7. The system of claim 1, wherein the processor is configured to receive the image from a camera positioned at the surgical site.

8. A robotic surgery system comprising:
a viewer; and
a processor configured to:
cause an image of at least a portion of a surgical site to be displayed on the viewer;
cause the viewer to display a graphical overlay; and
in response to a determination that a first instrument has been made available for use at the surgical site, cause the graphical overlay to include a first graphical representation corresponding to the first instrument.

9. The system of claim 8, wherein the processor is further configured to, in response to a determination that a second instrument has been made available for use at the surgical site, cause the graphical overlay to include a second graphical representation corresponding to the second instrument.

10. The system of claim 9, wherein the first graphical representation is displayed in a first region of the viewer and the second graphical representation is displayed in a second region of the viewer, the second region being different from the first region.

11. The system of claim 10, wherein the first region and the second region are positioned within a region occupied by the image on the viewer.

12. The system of claim 10, wherein the first graphical representation indicates that the first instrument is available for use at the surgical site and the second graphical representation indicates that the second instrument is available for use at the surgical site.

13. A robotic surgery system comprising:
a viewer; and
a processor configured to:
cause an image of at least a portion of a surgical site to be displayed on the viewer;
cause a graphical overlay to be displayed on the viewer; and
in response to a determination that a first instrument has been made available for use at the surgical site, cause a characteristic of the graphical overlay to change to represent the first instrument.

14. The system of claim 13, wherein the processor is configured to cause the characteristic of the graphical overlay to change to represent the first instrument by causing a portion of the graphical overlay to be emphasized.

15. The system of claim 14, wherein the portion of the graphical overlay comprises an icon graphically representing the first instrument.

16. The system of claim 13, wherein the characteristic indicates that the first instrument is available for use at the surgical site.

17. The system of claim 13, wherein the processor is further configured to, in response to a determination that a second instrument has been made available for use at the surgical site, cause the characteristic or a different characteristic of the graphical overlay to change to represent the second instrument.

18. The system of claim 17, wherein the processor is configured to cause the characteristic or the different characteristic of the graphical overlay to change to represent the second instrument by causing a portion of the graphical overlay to be emphasized.

19. The system of claim 18, wherein the portion of the graphical overlay comprises an icon graphically representing the second instrument.

20. The system of claim 17, wherein the different characteristic indicates that the second instrument is available for use at the surgical site.

* * * * *